United States Patent
Carroll et al.

(10) Patent No.: US 9,566,075 B2
(45) Date of Patent: Feb. 14, 2017

(54) PATIENT SPECIFIC SURGICAL GUIDE LOCATOR AND MOUNT

(71) Applicant: MicroPort Orthopedics Holdings Inc., Tiel (NL)

(72) Inventors: Michael Carroll, Memphis, TN (US); Richard Obert, Germantown, TN (US); Paul Stemniski, Arlington, TN (US)

(73) Assignee: MicroPort Orthopedics Holdings Inc., Tiel (NL)

( * ) Notice: Subject to any disclaimer, the term of this patent is extended or adjusted under 35 U.S.C. 154(b) by 442 days.

(21) Appl. No.: 13/919,091

(22) Filed: Jun. 17, 2013

(65) Prior Publication Data

US 2013/0274753 A1 Oct. 17, 2013

Related U.S. Application Data

(63) Continuation of application No. 12/710,898, filed on Feb. 23, 2010, now Pat. No. 9,017,334.

(Continued)

(51) Int. Cl.
| | | |
|---|---|---|
| *A61B 17/15* | (2006.01) | |
| *B29C 67/00* | (2006.01) | |

(Continued)

(52) U.S. Cl.
CPC ........... *A61B 17/151* (2013.01); *A61B 17/154* (2013.01); *A61B 17/155* (2013.01); *A61B 17/157* (2013.01); *A61B 34/10* (2016.02); *B29C 67/0088* (2013.01); *G05B 15/02* (2013.01); *G06F 17/50* (2013.01); *A61B 2017/0023* (2013.01); *A61B 2017/00526* (2013.01); *A61B 2017/568* (2013.01);

(Continued)

(58) Field of Classification Search
CPC .................................................. A61B 17/155
USPC .................................................. 606/86 R–90
See application file for complete search history.

(56) References Cited

U.S. PATENT DOCUMENTS

| | | |
|---|---|---|
| 3,314,420 A | 4/1967 | Smith et al. |
| 3,605,123 A | 9/1971 | Hahn |

(Continued)

FOREIGN PATENT DOCUMENTS

| | | |
|---|---|---|
| CN | 101111197 | 1/2008 |
| DE | 2306552 | 8/1974 |

(Continued)

OTHER PUBLICATIONS

Andersson, et al., "Macintosh Arthroplasty in Rheumatoid Arthritis," Acta. Orthrop. Scand., 1974, pp. 245-259, 45(2).

(Continued)

*Primary Examiner* — David Bates
*Assistant Examiner* — Olivia C Chang
(74) *Attorney, Agent, or Firm* — Adams and Reese LLP

(57) ABSTRACT

A resection guide locator includes a bone engagement portion with surfaces that are complementary to the surface topographies of a bone to be resected during surgery. A housing includes a socket defined by a resilient annular wall that is sized and arranged so to accept a resection guide by press-fit to thereby position and hold the resection guide within the socket. The resection guide is maintained in a predetermined, preferred position while the surfaces are releasably locked in position on the bone. A method is disclosed for forming and using the resection guide locator.

12 Claims, 28 Drawing Sheets

Related U.S. Application Data

(60) Provisional application No. 61/154,845, filed on Feb. 24, 2009.

(51) Int. Cl.

| | |
|---|---|
| G05B 15/02 | (2006.01) |
| G06F 17/50 | (2006.01) |
| A61B 17/00 | (2006.01) |
| A61B 17/56 | (2006.01) |
| B33Y 50/02 | (2015.01) |

(52) U.S. Cl.
CPC ... *A61B 2034/104* (2016.02); *A61B 2034/108* (2016.02); *B33Y 50/02* (2014.12); *Y10T 29/49* (2015.01); *Y10T 29/49863* (2015.01)

(56) References Cited

U.S. PATENT DOCUMENTS

| | | | |
|---|---|---|---|
| 3,798,679 A | 3/1974 | Ewald | |
| 3,808,606 A | 5/1974 | Tronzo | |
| 3,843,975 A | 10/1974 | Tronzo | |
| 3,855,638 A | 12/1974 | Pilliar | |
| 3,938,198 A | 2/1976 | Kahn et al. | |
| 3,987,499 A | 10/1976 | Scharbach et al. | |
| 4,052,753 A | 10/1977 | Dedo | |
| 4,055,862 A | 11/1977 | Farling | |
| 4,085,466 A | 4/1978 | Goodfellow et al. | |
| 4,098,626 A | 7/1978 | Graham et al. | |
| 4,203,444 A | 5/1980 | Bonnell et al. | |
| 4,213,816 A | 7/1980 | Morris | |
| 4,340,978 A | 7/1982 | Buechel et al. | |
| 4,368,040 A | 1/1983 | Weissman | |
| 4,436,684 A | 3/1984 | White | |
| 4,501,266 A | 2/1985 | McDaniel | |
| 4,502,161 A | 3/1985 | Wall | |
| 4,586,496 A | 5/1986 | Keller | |
| 4,594,380 A | 6/1986 | Chapin et al. | |
| 4,601,290 A | 7/1986 | Effron et al. | |
| 4,609,551 A | 9/1986 | Caplan et al. | |
| 4,627,853 A | 12/1986 | Campbell et al. | |
| 4,703,751 A | 11/1987 | Pohl | |
| 4,704,686 A | 11/1987 | Aldinger | |
| 4,715,860 A | 12/1987 | Amstutz et al. | |
| 4,721,104 A | 1/1988 | Kaufman et al. | |
| 4,759,350 A | 7/1988 | Dunn et al. | |
| 4,769,040 A | 9/1988 | Wevers | |
| 4,841,975 A | 6/1989 | Woolson | |
| 4,846,835 A | 7/1989 | Grande | |
| 4,865,607 A | 9/1989 | Witzel et al. | |
| 4,880,429 A | 11/1989 | Stone | |
| 4,936,862 A | 6/1990 | Walker et al. | |
| 4,979,949 A | 12/1990 | Matsen, III et al. | |
| 5,002,547 A | 3/1991 | Poggie et al. | |
| 5,041,138 A | 8/1991 | Vacanti et al. | |
| 5,059,216 A | 10/1991 | Winters | |
| 5,067,964 A | 11/1991 | Richmond et al. | |
| 5,122,144 A | 6/1992 | Bert et al. | |
| 5,129,908 A | 7/1992 | Petersen | |
| 5,133,759 A | 7/1992 | Turner | |
| 5,154,717 A | 10/1992 | Matsen, III et al. | |
| 5,162,430 A | 11/1992 | Rhee et al. | |
| 5,171,322 A | 12/1992 | Kenny | |
| 5,197,985 A | 3/1993 | Caplan et al. | |
| 5,206,023 A | 4/1993 | Hunziker | |
| 5,226,914 A | 7/1993 | Caplan et al. | |
| 5,234,433 A | 8/1993 | Bert et al. | |
| 5,250,050 A | 10/1993 | Poggie et al. | |
| 5,258,032 A | 11/1993 | Bertin | |
| 5,270,300 A | 12/1993 | Hunziker | |
| 5,288,797 A | 2/1994 | Khalil et al. | |
| 5,303,148 A | 4/1994 | Mattson et al. | |
| 5,306,311 A | 4/1994 | Stone et al. | |
| 5,314,482 A | 5/1994 | Goodfellow et al. | |
| 5,344,459 A | 9/1994 | Swartz | |
| 5,360,446 A | 11/1994 | Kennedy | |
| 5,365,996 A | 11/1994 | Crook | |
| 5,368,858 A | 11/1994 | Hunziker | |
| 5,370,692 A | 12/1994 | Fink et al. | |
| 5,380,332 A | 1/1995 | Ferrante | |
| 5,387,216 A | 2/1995 | Thornhill et al. | |
| 5,454,816 A | 10/1995 | Ashby | |
| 5,462,550 A | 10/1995 | Dietz et al. | |
| 5,468,787 A | 11/1995 | Braden et al. | |
| 5,474,559 A | 12/1995 | Bertin et al. | |
| 5,478,739 A | 12/1995 | Slivka et al. | |
| 5,486,180 A | 1/1996 | Dietz et al. | |
| 5,501,687 A | 3/1996 | Willert et al. | |
| 5,503,162 A | 4/1996 | Athanasiou et al. | |
| 5,523,843 A | 6/1996 | Yamane et al. | |
| 5,540,696 A | 7/1996 | Booth, Jr. et al. | |
| 5,542,947 A | 8/1996 | Treacy | |
| 5,554,190 A | 9/1996 | Draenert | |
| 5,556,432 A | 9/1996 | Kubein-Meesenburg et al. | |
| 5,571,205 A | 11/1996 | James | |
| 5,575,793 A | 11/1996 | Carls et al. | |
| 5,578,037 A | 11/1996 | Sanders et al. | |
| 5,593,450 A | 1/1997 | Scott et al. | |
| 5,597,379 A | 1/1997 | Haines et al. | |
| 5,601,563 A | 2/1997 | Burke et al. | |
| 5,613,970 A | 3/1997 | Houston et al. | |
| 5,616,146 A | 4/1997 | Murray | |
| 5,630,820 A | 5/1997 | Todd | |
| 5,632,745 A | 5/1997 | Schwartz | |
| 5,649,929 A | 7/1997 | Callaway | |
| 5,658,290 A | 8/1997 | Lechot | |
| 5,671,741 A | 9/1997 | Lang et al. | |
| 5,682,886 A | 11/1997 | Delp et al. | |
| 5,683,466 A | 11/1997 | Vitale | |
| 5,684,562 A | 11/1997 | Fujieda | |
| 5,688,282 A | 11/1997 | Baron et al. | |
| 5,728,162 A | 3/1998 | Eckhoff | |
| 5,735,277 A | 4/1998 | Schuster | |
| 5,749,874 A | 5/1998 | Schwartz | |
| 5,749,876 A | 5/1998 | Duvillier et al. | |
| 5,765,561 A | 6/1998 | Chen et al. | |
| 5,768,134 A | 6/1998 | Swaelens et al. | |
| 5,769,899 A | 6/1998 | Schwartz et al. | |
| 5,786,217 A | 7/1998 | Tubo et al. | |
| 5,798,924 A | 8/1998 | Eufinger et al. | |
| 5,800,438 A | 9/1998 | Tuke et al. | |
| 5,824,083 A | 10/1998 | Draenert | |
| 5,827,289 A | 10/1998 | Reiley et al. | |
| 5,830,216 A | 11/1998 | Insall et al. | |
| 5,835,619 A | 11/1998 | Morimoto et al. | |
| 5,842,477 A | 12/1998 | Naughton et al. | |
| 5,847,804 A | 12/1998 | Sarver et al. | |
| 5,853,746 A | 12/1998 | Hunziker | |
| 5,860,981 A | 1/1999 | Bertin et al. | |
| 5,871,018 A | 2/1999 | Delp et al. | |
| 5,871,542 A | 2/1999 | Goodfellow et al. | |
| 5,871,546 A | 2/1999 | Colleran et al. | |
| 5,879,390 A | 3/1999 | Kubein-Meesenburg et al. | |
| 5,880,976 A | 3/1999 | DiGioia, III et al. | |
| 5,885,296 A | 3/1999 | Masini | |
| 5,885,297 A | 3/1999 | Matsen, III | |
| 5,885,298 A | 3/1999 | Herrington et al. | |
| 5,897,559 A | 4/1999 | Masini | |
| 5,899,859 A | 5/1999 | Votruba et al. | |
| 5,900,245 A | 5/1999 | Sawhney et al. | |
| 5,906,934 A | 5/1999 | Grande et al. | |
| 5,911,723 A | 6/1999 | Ashby et al. | |
| 5,916,220 A | 6/1999 | Masini | |
| 5,939,323 A | 8/1999 | Valentini et al. | |
| 5,961,523 A | 10/1999 | Masini | |
| 5,968,051 A | 10/1999 | Luckman et al. | |
| 5,972,385 A | 10/1999 | Liu et al. | |
| 5,995,738 A | 11/1999 | DiGioia, III et al. | |
| 6,001,895 A | 12/1999 | Harvey et al. | |
| 6,002,859 A | 12/1999 | DiGioia, III et al. | |
| 6,006,126 A | 12/1999 | Cosman | |
| 6,007,537 A | 12/1999 | Burkinshaw et al. | |
| 6,010,509 A | 1/2000 | Delgado et al. | |
| 6,013,081 A | 1/2000 | Burkinshaw et al. | |

(56) References Cited

U.S. PATENT DOCUMENTS

| | | |
|---|---|---|
| 6,013,103 A | 1/2000 | Kaufman et al. |
| 6,046,379 A | 4/2000 | Stone et al. |
| 6,056,754 A | 5/2000 | Haines et al. |
| 6,056,756 A | 5/2000 | Eng et al. |
| 6,057,927 A | 5/2000 | Levesque et al. |
| 6,077,270 A | 6/2000 | Katz |
| 6,082,364 A | 7/2000 | Balian et al. |
| 6,090,144 A | 7/2000 | Letot et al. |
| 6,093,204 A | 7/2000 | Stone |
| 6,096,043 A | 8/2000 | Techiera et al. |
| 6,102,916 A | 8/2000 | Masini |
| 6,106,529 A | 8/2000 | Techiera |
| 6,110,209 A | 8/2000 | Stone |
| 6,120,541 A | 9/2000 | Johnson |
| 6,126,690 A | 10/2000 | Ateshian et al. |
| 6,139,578 A | 10/2000 | Lee et al. |
| 6,156,069 A | 12/2000 | Amstutz |
| 6,161,080 A | 12/2000 | Aouni-Ateshian et al. |
| 6,187,010 B1 | 2/2001 | Masini |
| 6,200,606 B1 | 3/2001 | Peterson et al. |
| 6,203,546 B1 | 3/2001 | MacMahon |
| 6,203,576 B1 | 3/2001 | Afriat et al. |
| 6,205,411 B1 | 3/2001 | DiGioia, III et al. |
| 6,206,927 B1 | 3/2001 | Fell et al. |
| 6,214,369 B1 | 4/2001 | Grande et al. |
| 6,217,894 B1 | 4/2001 | Sawhney et al. |
| 6,219,571 B1 | 4/2001 | Hargreaves et al. |
| 6,224,632 B1 | 5/2001 | Pappas et al. |
| 6,235,060 B1 | 5/2001 | Kubein-Meesenburg et al. |
| 6,251,143 B1 | 6/2001 | Schwartz et al. |
| 6,254,639 B1 | 7/2001 | Peckitt |
| 6,277,151 B1 | 8/2001 | Lee et al. |
| 6,281,195 B1 | 8/2001 | Rueger et al. |
| 6,283,980 B1 | 9/2001 | Vibe-Hansen et al. |
| 6,296,646 B1 | 10/2001 | Williamson |
| 6,299,905 B1 | 10/2001 | Peterson et al. |
| 6,322,588 B1 | 11/2001 | Ogle et al. |
| 6,327,491 B1 | 12/2001 | Franklin et al. |
| 6,328,765 B1 | 12/2001 | Hardwick et al. |
| 6,344,043 B1 | 2/2002 | Pappas |
| 6,344,059 B1 | 2/2002 | Krakovits et al. |
| 6,352,558 B1 | 3/2002 | Spector |
| 6,358,253 B1 | 3/2002 | Torrie et al. |
| 6,365,405 B1 | 4/2002 | Salzmann et al. |
| 6,371,958 B1 | 4/2002 | Overaker |
| 6,373,250 B1 | 4/2002 | Tsoref et al. |
| 6,375,658 B1 | 4/2002 | Hangody et al. |
| 6,379,367 B1 | 4/2002 | Vibe-Hansen et al. |
| 6,382,028 B1 | 5/2002 | Wooh et al. |
| 6,383,228 B1 | 5/2002 | Schmotzer |
| 6,387,131 B1 | 5/2002 | Miehlke et al. |
| 6,429,013 B1 | 8/2002 | Halvorsen et al. |
| 6,443,988 B2 | 9/2002 | Felt et al. |
| 6,443,991 B1 | 9/2002 | Running |
| 6,444,222 B1 | 9/2002 | Asculai et al. |
| 6,459,927 B1 | 10/2002 | Franklin et al. |
| 6,459,948 B1 | 10/2002 | Ateshian et al. |
| 6,468,314 B2 | 10/2002 | Schwartz et al. |
| 6,478,799 B1 | 11/2002 | Williamson |
| 6,479,996 B1 | 11/2002 | Hoogeveen et al. |
| 6,510,334 B1 | 1/2003 | Schuster et al. |
| 6,520,964 B2 | 2/2003 | Tallarida et al. |
| 6,558,421 B1 | 5/2003 | Fell et al. |
| 6,560,476 B1 | 5/2003 | Pelletier et al. |
| 6,575,980 B1 | 6/2003 | Robie et al. |
| 6,620,168 B1 | 9/2003 | Lombardo et al. |
| 6,626,945 B2 | 9/2003 | Simon et al. |
| 6,626,948 B2 | 9/2003 | Storer et al. |
| 6,632,225 B2 | 10/2003 | Sanford et al. |
| 6,632,235 B2 | 10/2003 | Weikel et al. |
| 6,652,587 B2 | 11/2003 | Felt et al. |
| 6,673,077 B1 | 1/2004 | Katz |
| 6,679,917 B2 | 1/2004 | Ek |
| 6,712,856 B1 | 3/2004 | Carignan et al. |
| 6,738,657 B1 | 5/2004 | Franklin et al. |
| 6,905,514 B2 | 6/2005 | Carignan et al. |
| 6,916,341 B2 | 7/2005 | Rolston |
| 6,928,742 B2 | 8/2005 | Broers et al. |
| 6,932,842 B1 | 8/2005 | Litschko et al. |
| 6,942,667 B1 | 9/2005 | Song |
| 6,944,518 B2 | 9/2005 | Roose |
| 6,969,393 B2 | 11/2005 | Pinczewski et al. |
| 6,980,849 B2 | 12/2005 | Sasso |
| 6,988,015 B1 | 1/2006 | Schopf et al. |
| 6,993,374 B2 | 1/2006 | Sasso |
| 7,008,430 B2 | 3/2006 | Dong et al. |
| 7,058,439 B2 | 6/2006 | Eaton et al. |
| 7,060,074 B2 | 6/2006 | Rosa et al. |
| 7,104,997 B2 | 9/2006 | Lionberger et al. |
| 7,115,131 B2 | 10/2006 | Engh et al. |
| 7,117,027 B2 | 10/2006 | Zheng et al. |
| 7,141,053 B2 | 11/2006 | Rosa et al. |
| 7,184,814 B2 | 2/2007 | Lang et al. |
| 7,201,762 B2 | 4/2007 | Greene, Jr. et al. |
| 7,217,276 B2 | 5/2007 | Henderson et al. |
| 7,239,908 B2 | 7/2007 | Alexander et al. |
| 7,245,697 B2 | 7/2007 | Lang |
| 7,282,054 B2 | 10/2007 | Steffensmeier et al. |
| 7,292,674 B2 | 11/2007 | Lang |
| 7,347,690 B2 | 3/2008 | Jordan et al. |
| 7,364,581 B2 | 4/2008 | Michalowicz |
| 7,377,924 B2 | 5/2008 | Raistrick et al. |
| 7,379,529 B2 | 5/2008 | Lang |
| 7,467,892 B2 | 12/2008 | Lang et al. |
| 7,468,075 B2 | 12/2008 | Lang et al. |
| 7,534,246 B2 | 5/2009 | Reiley et al. |
| 7,534,263 B2 | 5/2009 | Burdulis, Jr. et al. |
| 7,618,451 B2 | 11/2009 | Berez et al. |
| 7,747,305 B2 | 6/2010 | Dean et al. |
| 7,806,896 B1 | 10/2010 | Bonutti |
| 7,881,768 B2 | 2/2011 | Lang et al. |
| 7,981,158 B2 | 7/2011 | Fitz et al. |
| 7,983,777 B2 | 7/2011 | Melton et al. |
| 8,036,729 B2 | 10/2011 | Lang et al. |
| 8,062,302 B2 | 11/2011 | Lang et al. |
| 8,066,708 B2 | 11/2011 | Lang et al. |
| 8,083,745 B2 | 12/2011 | Lang et al. |
| 8,105,330 B2 | 1/2012 | Fitz et al. |
| 8,112,142 B2 | 2/2012 | Alexander et al. |
| 8,122,582 B2 | 2/2012 | Burdulis, Jr. et al. |
| RE43,282 E | 3/2012 | Alexander et al. |
| 8,337,503 B2 | 12/2012 | Lian |
| 8,715,362 B2 | 5/2014 | Reiley et al. |
| 2001/0001120 A1 | 5/2001 | Masini |
| 2001/0010023 A1 | 7/2001 | Schwartz et al. |
| 2001/0039455 A1 | 11/2001 | Simon et al. |
| 2002/0013626 A1 | 1/2002 | Geisllich et al. |
| 2002/0029038 A1 | 3/2002 | Haines |
| 2002/0045940 A1 | 4/2002 | Giannelli et al. |
| 2002/0059049 A1 | 5/2002 | Bradbury et al. |
| 2002/0068979 A1 | 6/2002 | Brown et al. |
| 2002/0072821 A1 | 6/2002 | Baker |
| 2002/0079601 A1 | 6/2002 | Russell et al. |
| 2002/0082703 A1 | 6/2002 | Repicci |
| 2002/0087274 A1 | 7/2002 | Alexander et al. |
| 2002/0106625 A1 | 8/2002 | Hung et al. |
| 2002/0115647 A1 | 8/2002 | Halvorsen et al. |
| 2002/0120274 A1 | 8/2002 | Overaker et al. |
| 2002/0120281 A1 | 8/2002 | Overaker |
| 2002/0123817 A1 | 9/2002 | Clasbrummel et al. |
| 2002/0127264 A1 | 9/2002 | Felt et al. |
| 2002/0133230 A1 | 9/2002 | Repicci |
| 2002/0143402 A1 | 10/2002 | Steinberg |
| 2002/0151986 A1 | 10/2002 | Asculai et al. |
| 2002/0156150 A1 | 10/2002 | Williams et al. |
| 2002/0156479 A1 | 10/2002 | Schulzki et al. |
| 2002/0173852 A1 | 11/2002 | Felt et al. |
| 2002/0183850 A1 | 12/2002 | Felt et al. |
| 2002/0198531 A1 | 12/2002 | Millard et al. |
| 2003/0028196 A1 | 2/2003 | Bonutti |
| 2003/0055500 A1 | 3/2003 | Fell et al. |
| 2003/0055501 A1 | 3/2003 | Fell et al. |
| 2003/0055502 A1 | 3/2003 | Lang et al. |
| 2003/0060882 A1 | 3/2003 | Fell et al. |

(56) References Cited

U.S. PATENT DOCUMENTS

| | | |
|---|---|---|
| 2003/0060883 A1 | 3/2003 | Fell et al. |
| 2003/0060884 A1 | 3/2003 | Fell et al. |
| 2003/0060885 A1 | 3/2003 | Fell et al. |
| 2003/0100907 A1 | 5/2003 | Rosa et al. |
| 2003/0100953 A1 | 5/2003 | Rosa et al. |
| 2003/0120347 A1 | 6/2003 | Steinberg |
| 2003/0158558 A1 | 8/2003 | Horn |
| 2003/0158606 A1 | 8/2003 | Coon et al. |
| 2003/0163137 A1 | 8/2003 | Smucker et al. |
| 2003/0173695 A1 | 9/2003 | Monkhouse et al. |
| 2003/0216669 A1 | 11/2003 | Lang et al. |
| 2003/0225457 A1 | 12/2003 | Justin et al. |
| 2003/0236521 A1 | 12/2003 | Brown et al. |
| 2004/0098133 A1 | 5/2004 | Carignan et al. |
| 2004/0102852 A1 | 5/2004 | Johnson et al. |
| 2004/0122521 A1 | 6/2004 | Lee et al. |
| 2004/0133276 A1 | 7/2004 | Lang et al. |
| 2004/0138754 A1 | 7/2004 | Lang et al. |
| 2004/0147927 A1 | 7/2004 | Tsougarakis et al. |
| 2004/0153079 A1 | 8/2004 | Tsougarakis et al. |
| 2004/0153162 A1 | 8/2004 | Sanford et al. |
| 2004/0153164 A1 | 8/2004 | Sanford et al. |
| 2004/0167390 A1 | 8/2004 | Alexander et al. |
| 2004/0167630 A1 | 8/2004 | Rolston |
| 2004/0193280 A1 | 9/2004 | Webster et al. |
| 2004/0204644 A1 | 10/2004 | Tsougarakis et al. |
| 2004/0204760 A1 | 10/2004 | Fitz et al. |
| 2004/0236424 A1 | 11/2004 | Berez et al. |
| 2004/0249386 A1 | 12/2004 | Faoro |
| 2005/0015153 A1 | 1/2005 | Goble et al. |
| 2005/0021039 A1 | 1/2005 | Cusick et al. |
| 2005/0043807 A1 | 2/2005 | Wood |
| 2005/0049603 A1 | 3/2005 | Calton et al. |
| 2005/0055028 A1 | 3/2005 | Haines |
| 2005/0085920 A1 | 4/2005 | Williamson |
| 2005/0107883 A1 | 5/2005 | Goodfried et al. |
| 2005/0107884 A1 | 5/2005 | Johnson et al. |
| 2005/0119664 A1 | 6/2005 | Carignan et al. |
| 2005/0143745 A1 | 6/2005 | Hodorek et al. |
| 2005/0148843 A1 | 7/2005 | Roose |
| 2005/0171545 A1 | 8/2005 | Walsh et al. |
| 2005/0171612 A1 | 8/2005 | Rolston |
| 2005/0192588 A1 | 9/2005 | Garcia |
| 2005/0216305 A1 | 9/2005 | Funderud |
| 2005/0234461 A1 | 10/2005 | Burdulis, Jr. et al. |
| 2005/0267584 A1 | 12/2005 | Burdulis et al. |
| 2006/0052795 A1 | 3/2006 | White |
| 2006/0111722 A1 | 5/2006 | Bouadi |
| 2006/0149283 A1 | 7/2006 | May et al. |
| 2006/0200162 A1 | 9/2006 | Farling et al. |
| 2006/0235421 A1 | 10/2006 | Rosa et al. |
| 2007/0015995 A1 | 1/2007 | Lang |
| 2007/0073305 A1 | 3/2007 | Lionberger et al. |
| 2007/0118141 A1 | 5/2007 | Marchyn et al. |
| 2007/0198022 A1 | 8/2007 | Lang et al. |
| 2007/0203430 A1 | 8/2007 | Lang et al. |
| 2007/0233151 A1 | 10/2007 | Chudik |
| 2007/0233156 A1 | 10/2007 | Metzger |
| 2007/0276224 A1 | 11/2007 | Lang et al. |
| 2007/0293868 A1 | 12/2007 | Delfosse et al. |
| 2008/0004709 A1 | 1/2008 | O'Neill et al. |
| 2008/0015433 A1 | 1/2008 | Alexander et al. |
| 2008/0025463 A1 | 1/2008 | Lang et al. |
| 2008/0031412 A1 | 2/2008 | Lang et al. |
| 2008/0058613 A1 | 3/2008 | Lang et al. |
| 2008/0058945 A1 | 3/2008 | Hajaj et al. |
| 2008/0114370 A1 | 5/2008 | Schoenefeld |
| 2008/0170659 A1 | 7/2008 | Lang et al. |
| 2008/0172056 A1 | 7/2008 | Edwards |
| 2008/0195109 A1* | 8/2008 | Hunter .................. A61B 17/155 606/87 |
| 2008/0195216 A1 | 8/2008 | Philipp |
| 2008/0219412 A1 | 9/2008 | Lang |
| 2008/0243127 A1 | 10/2008 | Lang |
| 2008/0255565 A1 | 10/2008 | Fletcher |
| 2008/0275452 A1 | 11/2008 | Lang et al. |
| 2008/0281328 A1 | 11/2008 | Lang et al. |
| 2008/0281329 A1 | 11/2008 | Lang et al. |
| 2008/0281426 A1 | 11/2008 | Fitz et al. |
| 2008/0287953 A1 | 11/2008 | Sers |
| 2009/0024131 A1 | 1/2009 | Metzger et al. |
| 2009/0076371 A1 | 3/2009 | Lang et al. |
| 2009/0087276 A1 | 4/2009 | Rose |
| 2009/0088753 A1* | 4/2009 | Aram .................. A61B 17/155 606/79 |
| 2009/0088758 A1 | 4/2009 | Bennett |
| 2009/0099567 A1 | 4/2009 | Zajac |
| 2009/0131941 A1 | 5/2009 | Park et al. |
| 2009/0131942 A1 | 5/2009 | Aker et al. |
| 2009/0222014 A1 | 9/2009 | Bojarski et al. |
| 2009/0307893 A1 | 12/2009 | Burdulis, Jr. et al. |
| 2010/0160917 A1 | 6/2010 | Fitz et al. |
| 2010/0262150 A1 | 10/2010 | Lian |
| 2010/0281678 A1 | 11/2010 | Burdulis, Jr. et al. |
| 2010/0298894 A1 | 11/2010 | Bojarski et al. |
| 2010/0305573 A1 | 12/2010 | Fitz et al. |
| 2010/0305574 A1 | 12/2010 | Fitz et al. |
| 2011/0066193 A1 | 3/2011 | Lang et al. |
| 2011/0071581 A1 | 3/2011 | Lang et al. |
| 2011/0213368 A1 | 9/2011 | Fitz et al. |
| 2011/0213373 A1 | 9/2011 | Fitz et al. |
| 2011/0213374 A1 | 9/2011 | Fitz et al. |
| 2011/0213377 A1 | 9/2011 | Lang et al. |
| 2011/0213427 A1 | 9/2011 | Fitz et al. |
| 2011/0213428 A1 | 9/2011 | Fitz et al. |
| 2011/0213429 A1 | 9/2011 | Lang et al. |
| 2011/0213430 A1 | 9/2011 | Lang et al. |
| 2011/0213431 A1 | 9/2011 | Fitz et al. |
| 2011/0218539 A1 | 9/2011 | Fitz et al. |
| 2011/0218584 A1 | 9/2011 | Fitz et al. |
| 2011/0230888 A1 | 9/2011 | Lang et al. |
| 2011/0238073 A1 | 9/2011 | Lang et al. |
| 2011/0313423 A1 | 12/2011 | Lang et al. |
| 2011/0319897 A1 | 12/2011 | Lang et al. |
| 2011/0319900 A1 | 12/2011 | Lang et al. |
| 2012/0029520 A1 | 2/2012 | Lang et al. |
| 2012/0041446 A1 | 2/2012 | Wong et al. |
| 2012/0066892 A1 | 3/2012 | Lang et al. |
| 2012/0071881 A1 | 3/2012 | Lang et al. |
| 2012/0071882 A1 | 3/2012 | Lang et al. |
| 2012/0071883 A1 | 3/2012 | Lang et al. |
| 2012/0072185 A1 | 3/2012 | Lang et al. |
| 2012/0101503 A1 | 4/2012 | Lang et al. |
| 2012/0143197 A1 | 6/2012 | Lang et al. |
| 2012/0151730 A1 | 6/2012 | Fitz et al. |
| 2012/0158001 A1 | 6/2012 | Burdulis, Jr. et al. |

FOREIGN PATENT DOCUMENTS

| | | |
|---|---|---|
| DE | 3516743 | 11/1986 |
| DE | 44 34 539 | 4/1996 |
| DE | 20303498 | 8/2003 |
| DE | 202008017199 U1 | 3/2009 |
| DE | 202008017200 U1 | 3/2009 |
| EP | 0377901 | 10/1989 |
| EP | 0528080 | 2/1993 |
| EP | 0530804 | 10/1993 |
| EP | 0626156 | 11/1994 |
| EP | 0704193 | 4/1996 |
| EP | 0896825 | 2/1999 |
| EP | 0938869 A2 | 9/1999 |
| EP | 0613380 | 12/1999 |
| EP | 0993807 | 4/2000 |
| EP | 1074229 | 2/2001 |
| EP | 1077253 | 2/2001 |
| EP | 1120087 | 8/2001 |
| EP | 1129675 | 9/2001 |
| EP | 1132061 | 9/2001 |
| EP | 0732091 | 12/2001 |
| EP | 0814731 | 8/2002 |
| EP | 1234552 | 8/2002 |
| EP | 1234555 | 8/2002 |
| EP | 0809987 | 10/2002 |
| EP | 0833620 | 10/2002 |

(56) References Cited

FOREIGN PATENT DOCUMENTS

| | | |
|---|---|---|
| FR | 2819714 | 7/2002 |
| GB | 1451283 | 9/1976 |
| GB | 2291355 | 1/1996 |
| GB | 2348373 | 10/2000 |
| JP | 8-173465 | 7/1996 |
| JP | 9-206322 | 8/1997 |
| JP | 2002-102236 | 4/2002 |
| JP | 2008-537689 A | 9/2008 |
| WO | WO 87/02882 | 5/1987 |
| WO | WO 90/09769 | 9/1990 |
| WO | WO 93/04710 | 3/1993 |
| WO | WO 93/09819 | 5/1993 |
| WO | WO 93/25157 | 12/1993 |
| WO | WO 95/27450 | 10/1995 |
| WO | WO 95/28688 | 10/1995 |
| WO | WO 95/30390 | 11/1995 |
| WO | WO 95/32623 | 12/1995 |
| WO | WO 96/24302 | 8/1996 |
| WO | WO 97/25942 | 7/1997 |
| WO | WO 97/26847 | 7/1997 |
| WO | WO 97/27885 | 8/1997 |
| WO | WO 97/38676 | 10/1997 |
| WO | WO 98/12994 | 4/1998 |
| WO | WO 98/20816 | 5/1998 |
| WO | WO 98/30617 | 7/1998 |
| WO | WO 98/32384 | 7/1998 |
| WO | WO 99/02654 | 1/1999 |
| WO | WO 99/08598 | 2/1999 |
| WO | WO 99/08728 | 2/1999 |
| WO | WO 99/42061 | 8/1999 |
| WO | WO 99/47186 | 9/1999 |
| WO | WO 99/51719 | 10/1999 |
| WO | WO 99/56674 | 11/1999 |
| WO | WO 00/09179 | 2/2000 |
| WO | WO 00/15153 | 3/2000 |
| WO | WO 00/35346 | 6/2000 |
| WO | WO 00/48550 | 8/2000 |
| WO | WO 00/59411 | 10/2000 |
| WO | WO 00/74554 | 12/2000 |
| WO | WO 01/10356 | 2/2001 |
| WO | WO 01/17463 | 3/2001 |
| WO | WO 01/19254 | 3/2001 |
| WO | WO 01/35968 | 5/2001 |
| WO | WO 01/45764 | 6/2001 |
| WO | WO 01/68800 | 9/2001 |
| WO | WO 01/70142 | 9/2001 |
| WO | WO 01/91672 | 12/2001 |
| WO | WO 02/00270 | 1/2002 |
| WO | WO 02/00275 | 1/2002 |
| WO | WO 02/02158 | 1/2002 |
| WO | WO 02/22013 | 3/2002 |
| WO | WO 02/22014 | 3/2002 |
| WO | WO 02/23483 | 3/2002 |
| WO | WO 02/34310 | 5/2002 |
| WO | WO 02/36147 | 5/2002 |
| WO | WO 02/096268 | 12/2002 |
| WO | WO 03/007788 | 1/2003 |
| WO | WO 03/037192 | 5/2003 |
| WO | WO 03/047470 | 6/2003 |
| WO | WO 03/051210 | 6/2003 |
| WO | WO 03/055400 | 7/2003 |
| WO | WO 2004/043305 | 5/2004 |
| WO | WO 2004/049981 | 6/2004 |
| WO | WO 2005/051239 | 6/2005 |
| WO | WO 2005/051240 | 6/2005 |
| WO | WO 2006/060795 | 6/2006 |
| WO | WO 2006/127283 | 11/2006 |
| WO | WO 2007/041375 | 4/2007 |
| WO | 2007/061983 A2 | 5/2007 |
| WO | WO 2007/092841 | 8/2007 |
| WO | WO 2008/112996 | 9/2008 |
| WO | 2008/138137 A1 | 11/2008 |
| WO | WO 2008/157412 | 12/2008 |
| WO | WO 2009/001083 | 12/2008 |
| WO | WO 2009/111639 | 9/2009 |
| WO | WO 2010/121147 | 10/2010 |
| WO | 2011/110374 A1 | 9/2011 |

OTHER PUBLICATIONS

Argenson, et al., "Is There a Place for Patellofemoral Arthroplasty?," "Clinical Orthopaedics and Related Research No. 321, 1995, pp. 162-167.

Birnbaum, et al., "Computer-Assisted Orthopedic Surgery with Individual Templates and Comparison to Conventional Operation Method," Spine, Feb. 2001, pp. 365-369, vol. 26, No. 4.

Chelule, et al., "Computer Aided Design of Personalized Jigs in Total Knee Replacement," 3rd Annual Meeting of CAOS Int'l Proc., Jun. 18-21, 2003, pp. 58-59, Spain.

Dare, S., Bobyn, J., Drouin, G., Dussault, R., Gariepy, R., "Use of Computerized Tomography and Numerical Control Machining for the Fabrication of Custom Arthroplasty Prostheses." Second World Congress on Biomaterials, 10th Annual Meeting of the Society for Biomaterials, p. 233, Washington, D.C., Apr. 27-May 1, 1984.

De Winter, et al., "The Richards Type II Patellofemoral Arthroplasty," Acta Orthop Scand, 2001, pp. 487-490, 72(5).

Delp, et al., "A Graphics-Based Software System to Develop and Analyze Models of Musculoskeletal Structures," Comput. Biol. Med., 1995, pp. 21-34, vol. 25, No. 1.

Farrar, et al., "Computed Tomography Scan Scout Film for Measurement of Femoral Axis in Knee Arthroplasty," J. Arthroplasty, 1999, pp. 1030-1031, vol. 14, No. 8.

Final Official Action for U.S. Appl. No. 13/465,547, dated Feb. 26, 2014.

First Office Action for Japanese Patent Appln. No. 2011-552091, dated Oct. 25, 2013.

Froemel, et al., "Computer Assisted Template Based Navigation for Total Knee Replacement," Documents presented at CAOS on Jun. 17, 2001, 4 pages.

Hafez, et al., "Computer Assisted Total Knee Replacement: Could a Two-Piece Custom Template Replace the Complex Conventional Instrumentations?", 4th Annual Meeting of CAOS Int'l Proc., Jun. 16-19, 2004, pp. 63-64, Chicago.

Hafez, et al., "Computer-Assisted Total Hip Arthroplasty: The Present and the Future," Future Rheumatol., 2006, pp. 121-131, vol. 1.

Kim, et al., "Measurement of Femoral Neck Anteversion in 3D. Part 1: 3D Imaging Method," Med. and Biol. Eng. and Computing, 2000, pp. 603-609, vol. 38, No. 6.

Lam, et al., "X-Ray Diagnosis: A Physician's Approach," 1998, Title page and Table of Contents pages Only, ISBN 9813083247, Springer-Verlag publishers.

Lam. et al.. "Varus\Valgus Alignment of the Femoral Component in Total Knee Arthroplasty," The Knee, 2003, pp. 237-241, vol. 10.

Lu, et al., "In Vitro Degradation of Porous poly(L-lactic acid) Foams," Biomaterials, Aug. 2000, pp. 1595-1605, 21(15).

Marler, et al., "Soft-Tissue Augmentation with Injectable Alginate and Synegeneic Fibroblasts," Plastic & Reconstructive Surgery, May, 2000 pp. 2049-2058, 105(6).

PCT/US2010/025143, International Preliminary Report on Patentability and Written Opinion, Sep. 9, 2011.

Portheine, "Model-Based Operation Planning in Orthopedic Surgery," Thesis, Apr. 22, 2004, 90 pages, RWTH Aachen University, in German.

Portheine, "Model-Based Operation Planning in Orthopedic Surgery," Thesis, Apr. 22, 2004, 170 pages, RWTH Aachen University, English Translation with Certification.

Portheine, et al., "Potentials of CT-based Planning and Template-based Procedure in Hip and Knee Surgery," Orth. Prac., 2000, pp. 786-791, vol. 36, English Translation with Certification.

Portheine. et al.. "Potentials of CT-based Planning and Template-based Procedure in Hip and Knee Surgery," Orth. Prac., 2000, pp. 786-791, vol. 36, in German.

Radermacher, "Computer Assisted Matching of Planning and Execution in Orthopedic Surgery," Slide Presentation, Nov. 29, 1993, 22 pages.

(56) References Cited

OTHER PUBLICATIONS

Radermacher, "Computer-Based Decision Support in the Selection and Evaluation of Contact Surfaces for Manual Referencing," Lecture presented at Helmholtz Meeting '98 and OSS '98, 7 pages, in German.

Radermacher, "Computer-Based Decision Support in the Selection and Evaluation of Contact Surfaces for Manual Referencing," Lecture presented at Helmholtz Meeting '98 and OSS '98, 8 pages, English Translation with Certifications.

Radermacher, "Image Guided Orthopedic Surgery with Individual Templates," Helmholtz-Institute for Biomed. Eng., 1997, 2 pages.

Radermacher, "Template Based Navigation- an Efficient Technique for Hip and Knee Surgery," CAOS First Asian Meet, Mar. 27-28, 2004, pp. 45-50, India.

Radermacher, et al., "Computer Assisted Matching of Planning and Execution in Orthopedic Surgery," IEEE, EMBS, 1993, pp. 946-947, San Diego.

Radermacher, et al., "Computer Integrated Advanced Orthopedics (CIAO)," 2nd European Conference on Eng. and Med., Apr. 26, 1993, 12 pages.

Radermacher, et al., "Computer Integrated Surgery—Connecting Planning and Execution of Surgical Intervention in Orthopedics," Surgical Therapy Technology, Helmholtz-Institut Aachen Research Report, 1991-1992, pp. 187, 196-202.

Radermacher, et al., "Computer-Assisted Operative Interventions in Orthopedics—Are There Prospects for Endoprosthetics As Well?", Prac. Ortho., 1997, pp. 149-164, vol. 27, in German.

Radermacher, et al., "Computer-Assisted Planning and Operation in Orthopedics," Orth. Prac. 36th Year, Dec. 2000, pp. 731-737, English Translation with Certification.

Radermacher, et al., "Surgical Therapy Technology," Helmholtz-Institut Aaachen Research Report, 1993-1994, pp. 189-219.

Radermacher. et al.. "Computer-Assisted Operative Interventions in Orthopedics—Are There Prospects for Endoprosthetics As Well?". Prac. Ortho., 1997, pp. 1-17, vol. 27, English Translation with Certification.

Radermacher. et al.. "Computer-Assisted Planning and Operation in Orthopedics," Orth. Prac. 36th Year, Dec. 2000, pp. 731-737, in German.

Rau, et al., "Small and Neat," Medical Tech. Int'l, 1993-1994, pp. 65, 67 and 69.

Schkommadau, et al., "Clinical Application of Individual Templates for Pedicle Screw Placement in Comparison to Computer Navigation," Poster presented at CAOS, Feb. 18, 2000, 1 page.

Schkommadau, et al., "Clinical Experience With the Individual Template Technique," Orth. Prac., 2001, pp. 19-22, vol. 37, No. 1, in German.

Schkommadau, et al., "Clinical Experience With the Individual Template Technique," Orth. Prac., 2001, pp. 19-22, vol. 37, No. 1, English Translation with Certification.

Seel, et al., "Three-Dimensional Planning and Virtual Radiographs in Revision Total Hip Arthroplasty for Instability," Clinical Orthopaedics and Related Research, Jan. 2006, pp. 35-38, No. 442.

Slone, et al., "Body CT: A Practical Approach," 1999, Title page And Table of Contents pages Only, ISBN 007058219, McGraw-Hill.

Staudte, et al., "Computer-Assisted Operation Planning and Technique in Orthopedics," North Rhine-Westphalia Acad. for Sciences, Lecture N.444, 2000, 17 pages, ISSN 0944-8799, in German.

Staudte, et al., "Computer-Assisted Operation Planning and Technique in Orthopedics," North Rhine-Westphalia Acad. for Sciences, Lecture N.444, 2000, 34 pages, ISSN 0944-8799, English Translation with Certification.

Stauffer, et al., "The Macintosh Prosthesis. Prospective Clinical and Gait Evaluation," Arch. Surg., 1975, pp. 717-720, 110(6).

Stout, et al., "X-Ray Structure Determination: A Practical Guide," 1989, Title page and Table of Contents pages Only, ISBN 0471607118, John Wiley & Sons.

Tamez-Pena, et al., "MRIIsotropic Resolution Reconstruction from Two Orthogonal Scans," Proceedings of the SPIE—The International Society for Optical Engineering SOIE-OMT, 2001, pp. 87-97, vol. 4322.

Testi, et al., "Border Tracing Algorithm Implementation for the Femoral Geometry Reconstruction," Camp. Meth. and Programs in Biomed., 2001, pp. 175-182, vol. 65.

Vandeberg, et al., "Assessment of Knee Cartilage in Cadavers with Dual-Detector Spiral CT Arthrography and MR Imaging," Radiology, Feb. 2002, pp. 430-435, 222(2).

Wiese, et al., "Biomaterial Properties and Biocompatibility in Cell Culture of a Novel Self-Inflating Hydrogel Tissue Expander," J. Biomedical Materials Research Part A, Nov. 2000, pp. 179-188, 54(2).

Woolson, S., Fellingham, L., Dev, P., and Vassiliadis, A., "Three Dimensional Imaging of Bone from Analysis of Computed Tomography Data." Orthopedics, vol. 8, No. 10, pp. 1269-1273, Oct. 1985.

Yusof, et al., "Preparation and Characterization of Chitin Beads as a Wound Dressing Precursor," J. Biomedical Materials Research Part A, Oct. 2000, pp. 59-68, 54(1).

In the United States Patent and Trademark Office: Final Office Action issued for U.S. Appl. No. 12/711,307, Feb. 4, 2015, 17 pages.

English translation of the Final Office Action dated Apr. 15, 2014, that issued in connection with Japanese patent application No. 2011-552091.

* cited by examiner

PATIENT SPECIFIC SURGICAL GUIDE LOCATOR AND MOUNT

RELATED APPLICATIONS

This application is a continuation of co-pending U.S. patent application Ser. No. 12/710,898, filed Feb. 23, 2010 which claims the benefit of U.S. Provisional Patent Application Ser. No. 61/154,845, filed Feb. 24, 2009, all of which are incorporated herein by reference in their entireties.

FIELD OF THE INVENTION

The present invention generally relates to surgical guides, and the fixtures used to locate such guides in relation to a patient's body during orthopedic procedures, such as, total knee, hip, or ankle replacement surgery, and methods for designing and using such instrument locators.

BACKGROUND OF THE INVENTION

Total joint (knee, hip, and ankle) replacement prostheses are known in the art. In many instances, a specially designed jig or fixture enables the surgeon to make accurate and precise bone resections of the femoral surface, the tibial surface, or both in order to accept such prostheses. The ultimate goal with any total joint prosthesis is to approximate the function of the natural, healthy structures that the prosthesis is replacing. Should the prosthesis not be properly attached to the femur, tibia, ankle or foot, any misalignment could result in discomfort to the patient, gate problems, or degradation of the prosthesis.

For example, when attaching a knee prosthesis it is desirable to orient the prosthesis such that the pivot axis of the knee joint lies within a transverse plane that is generally oriented perpendicular to the mechanical axis of the femur. The mechanical axis lies along a line which intersects the femoral head and the center of the ankle. In the prior art, the mechanical axis had been determined from an inspection of a radiograph of the femur to be resected prior to, or even during the surgery. During the actual operation, the mechanical axis was determined by computing its valgus angle from the femoral shaft axis. It was then necessary to manually align any cutting guide and its fixtures with respect to the femoral shaft axis in order to achieve an optimum cut.

Often such cutting guides included a femoral intramedullary stem which was inserted through a pre-drilled passage way formed in the intercondylar notch and upwardly through the femur along the femoral shaft axis. The stem often included a bracket which supports a distal femur cutting guide. The bracket included a first pin which extended through the cutting guide to act as a pivot axis. A second pin was attached to the bracket so as to extend through an arcuate slot in the cutting guide. The cutting guide included pairs of opposing slots formed along its sides which were oriented to be perpendicular to a central axis of symmetry of the cutting guide. When the cutting guide was pivoted, such that the central axis of symmetry lay along the mechanical axis, so as to form the appropriate angle with the femoral shaft axis, the cutting guide slots were positioned to be perpendicular to the mechanical axis. The cutting guide was then locked into the predetermined angle with the femoral shaft axis.

In more recent times, computer-aided design techniques have been coupled with advances in imaging technology to improve joint replacement prostheses and methods. For example, in U.S. Pat. No. 5,735,277, a process of producing an endoprosthesis for use in joint replacement is disclosed in which a reference image for determining contour differences on a femur and a tibia, are obtained by comparing a corrected preoperative image of a damaged knee joint with a postoperative image. This technique is then used as the basis for preparing corresponding femoral and tibial components of an endoprosthesis.

In U.S. Pat. No. 6,944,518, a method for making a joint prosthesis is provided in which computed tomography, commonly known as a CAT scan (CT) data from a patient's joint is used to design a prosthesis. The CT data is downloaded into a computer aided design software in order to design at least an attachment part, and possibly a functional part, of the prosthesis. The attachment part can be used to attach or otherwise associate the functional part to the patient's bone.

In U.S. Pat. No. 5,370,692, a method for producing prosthetic bone implants in which imaging technology is used to define hard tissue characteristics (size, shape, porosity, etc.) before a trauma occurs ("pre-trauma" file) by archival use of available imaging techniques (computed tomography, magnetic resonance imaging, or the like). Loss of hard tissue is determined by imaging in the locale of the affected tissue after the injury ("post-trauma" file). The physical properties of the customized prosthetic device are specified by comparison of the pre-trauma and post-trauma files to produce a solid model "design" file. This specification may also involve secondary manipulation of the files to assist in surgical implantation and to compensate for anticipated healing process. The design file is mathematically processed to produce a "sliced file" that is then used to direct a manufacturing system to construct a precise replica of the design file in a biocompatible material to produce the implant.

In U.S. Pat. No. 5,798,924, a method for producing endoprosthesis where a data block of a three-dimensional actual model of existing bone structure of a patient is acquired using CT scanning. In a computer, the actual model is subtracted from the data block of an existing or CT scan-generated three-dimensional reference model. Then from the difference, a computer-internal model for the endoprosthesis is formed. The data blocks of the actual model and reference model are converted into the data of a CAD free-form surface geometry.

None of the forgoing methods or devices have adequately provided surgeons with a way to generate patient specific prostheses, surgical instruments, guides, and fixtures, nor have they aided in reducing the number or complexity of the fixtures used to locate resection guides in relation to the patient's body during orthopedic procedures, such as, total knee, hip, or ankle replacement surgery.

SUMMARY OF THE INVENTION

The present invention provides a resection guide locator including a bone engagement portion having a surface topographically complementary to the surface contours of a bone to be resected during a surgical procedure. A socket is defined in a housing that is attached to the engagement portion. A resilient wall of the resection guide locator defines the peripheral extent of said socket, and is sized and shaped for storing energy when a resection guide is press-fit into the socket. In use during surgery, the resection guide operatively engages a portion of the wall so as to maintain the guide in position while the surface of the bone engagement portion is releasably locked to the bone.

In another embodiment of the invention, a resection guide locator is provided that includes a bone engagement portion with two surfaces that are complementary to respective separate surface topographies of a bone to be resected during surgery. A housing portion is attached to the bone engaging portion, and includes a socket defined by a resilient annular wall that is sized and arranged so to accept a resection guide by press-fit to thereby position and hold the resection guide within the socket. In this way, the resection guide is maintained in a predetermined, preferred position while the two surfaces are releasably locked in position on the bone.

In a further embodiment, a resection guide locator is provided that includes a base sized to engage a portion of a bone to be resected during surgery. The base has at least one surface that is topographically complementary to the surface topography of the bone. A housing that is attached to the base comprises a socket defined by a resilient peripheral wall arranged for storing energy when a resection guide is press-fit into the socket so as to operatively engage the wall. This arrangement maintains the guide in a predetermined position relative to the bone while the topographically complementary surface of the bone engagement portion is releasably locked onto the bone.

A method for forming and positioning a resection guide is also provided in which an anatomically accurate image of a bone is generated that includes surface topographies of the bone. The anatomically accurate image is converted to a digital model, and a digital representation of a resection guide locator is added to the digital model so as to form a composite digital model. Once the surface topographies complementarily mapped onto a bone engagement portion of the resection guide locator prior to manufacturing the resection guide locator based upon the composite digital model so that a manufactured resection guide locator is formed including the complementary surface topography on a bone engagement portion and a receptacle pocket sized to receive a resection guide with a press-fit. The resection guide locator is applied to the bone such that the complementary surface topography releasably locks the bone engagement portion to a corresponding portion of the bone.

BRIEF DESCRIPTION OF THE DRAWINGS

These and other features and advantages of the present invention will be more fully disclosed in, or rendered obvious by, the following detailed description of the preferred embodiment of the invention, which is to be considered together with the accompanying drawings wherein like numbers refer to like parts and further wherein.

DETAILED DESCRIPTION OF THE PREFERRED EMBODIMENT

Figure 1:
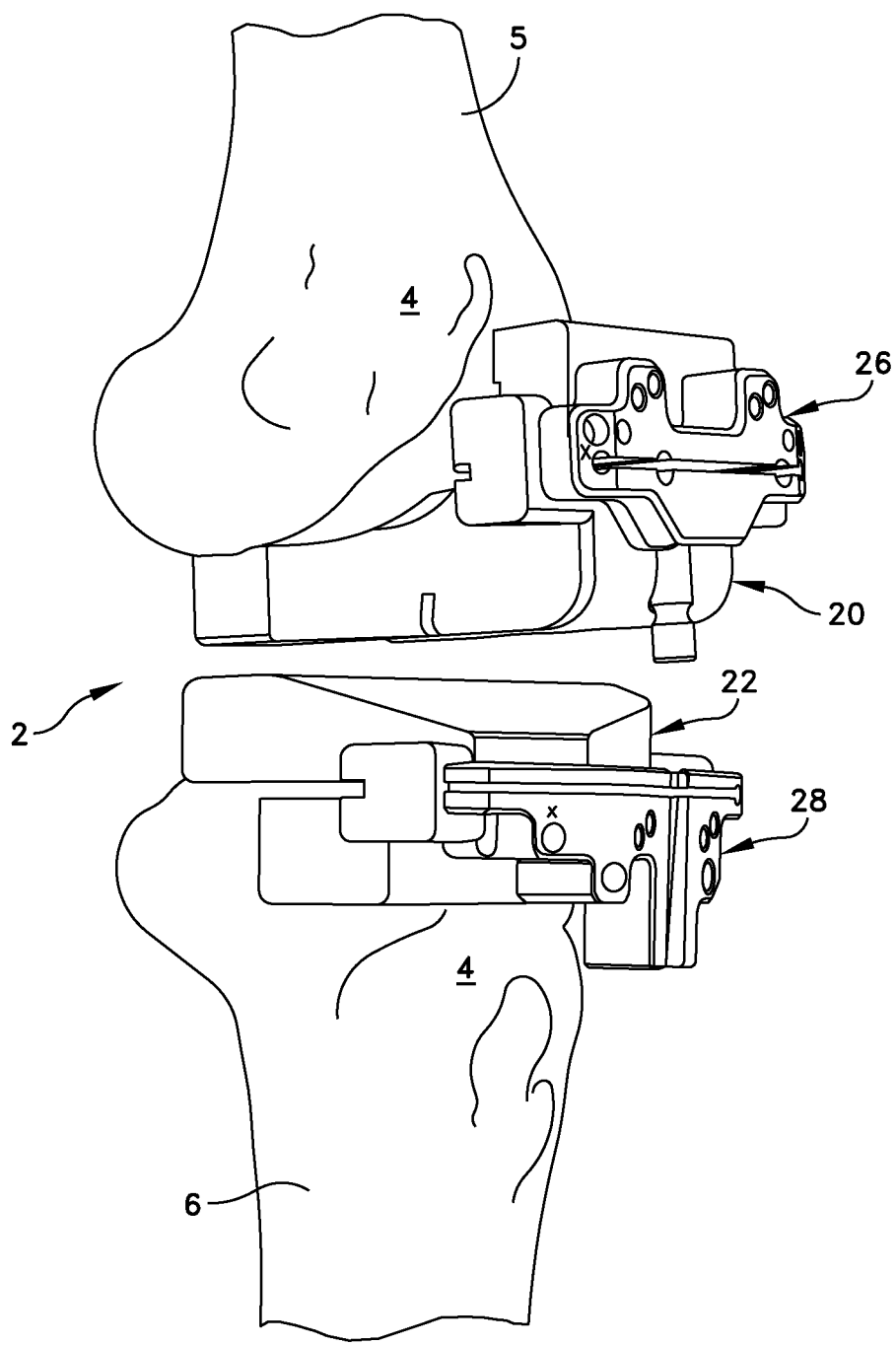
FIG. 1 is a perspective view of femoral and tibial resection guides mounted within resection guide locators that have been formed in accordance with the present invention and located upon portions of a femur and a tibia, respectively.

This description of preferred embodiments is intended to be read in connection with the accompanying drawings, which are to be considered part of the entire written description of this invention. The drawing figures are not necessarily to scale and certain features of the invention may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. When only a single machine is illustrated, the term "machine" shall also be taken to include any collection of machines that individually or jointly execute a set (or multiple sets) of instructions to perform any one or more of the methodologies discussed herein. The term "operatively connected" is such an attachment, coupling or connection that allows the pertinent structures to operate as intended by virtue of that relationship. In the claims, means-plus-function clauses, if used, are intended to cover the structures described, suggested, or rendered obvious by the written description or drawings for performing the recited function, including not only structural equivalents but also equivalent structures.

Figure 2:
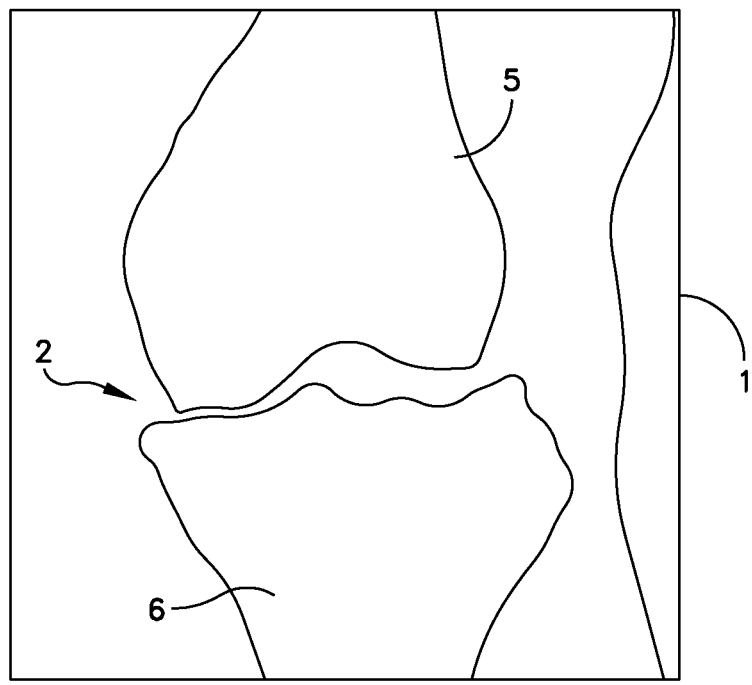
FIG. 2 is a schematic representation of a scanned image of a human knee joint.
Figure 3:
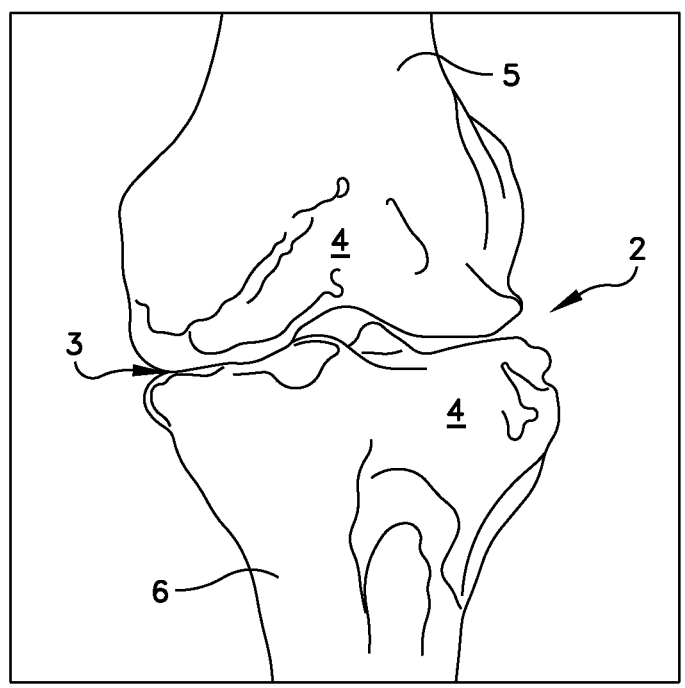
FIG. 3 is a schematic representation of the scanned image of the human knee joint shown in FIG. 2, after conversion to a computer model in accordance with the present invention.

The present invention provides custom manufactured surgical instruments, guides, and fixtures that are based upon a patient's anatomy as determined by a computer tomography scanner (CT), magnetic resonance imaging machine (MRI), or the like medical imaging technology. For example, a CT or MRI scanned image 1 or series of images may be taken of a patient's knee 1 or ankle 1a, including portions of the limb from the pelvis or the foot (FIGS. 2 and 3). In the case of a total knee replacement, the CT or MRI scanned image data is then converted from, e.g., a DICOM image format, to a solid computer model 3 of the lower limb often including the pelvis, femur, patella, tibia, or foot to determine implant alignment, type and sizing using specialized modeling methods that are often embodied in computer software. Computer generated solid models 3 that are derived from CT or MRI scan image data 1 will often include precise and accurate information regarding the surface contours surrounding the structures that have been imaged, e.g., the surface topography of the bones or contour of fascia that have been imaged. It will be understood that by surface topography it is meant the location, shape, size and distribution of surface features such as concavities and prominences or the like.

The methods disclosed in U.S. Pat. No. 5,768,134, issued to Swaelens et al., and incorporated herein by reference, have been found to yield adequate conversions of CT or MRI scanned image data 1 to solid computer model 3 usable with the present invention. In some embodiments, images are made of a lower limb, i.e., the pelvis, femur, patella, tibia, and/or foot of a patient using a CT or MRI machine, or other digital image capturing and processing unit (FIGS. 2 and 3). This scanning generates a scanned image of the diseased knee or ankle joint, including adjoining portions of the femur 5 and tibia 6. The image data 1 is first processed in a processing unit, after which a model is generated using the processed digitized image data.

Figure 4:
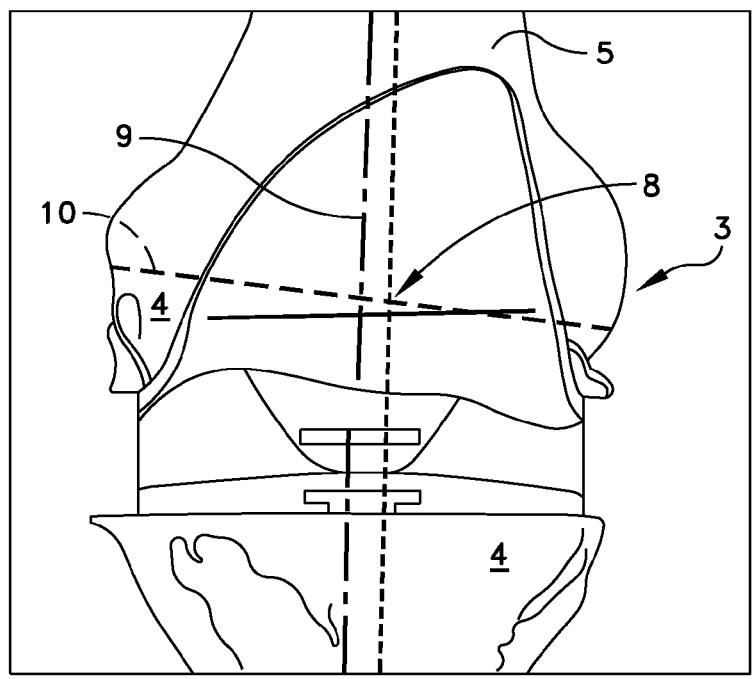
FIG. 4 is a schematic representation, similar to FIG. 3, showing proposed resection lines and local coordinates superpositioned upon the computer model of FIG. 3, in accordance with the present invention.
Figure 5:
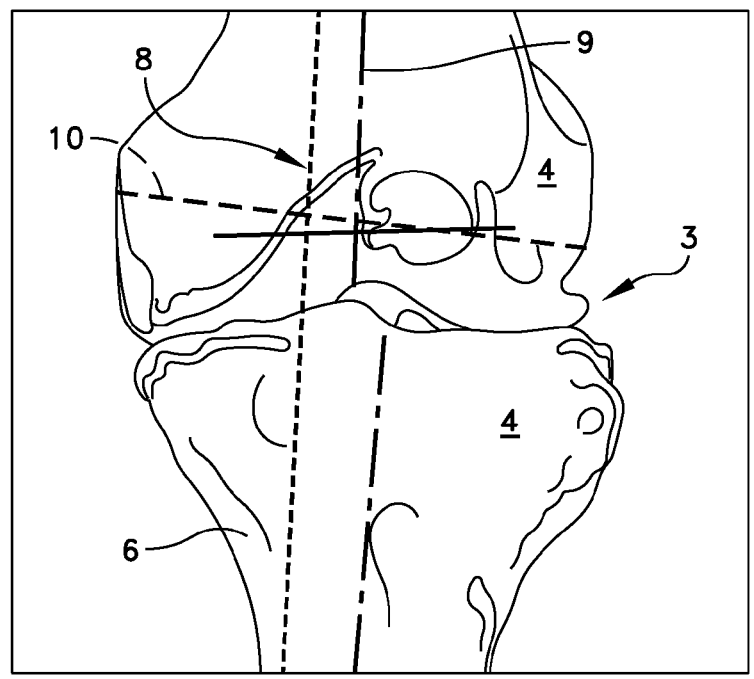
FIG. 5 is a schematic representation similar to FIG. 4.
Figure 7:
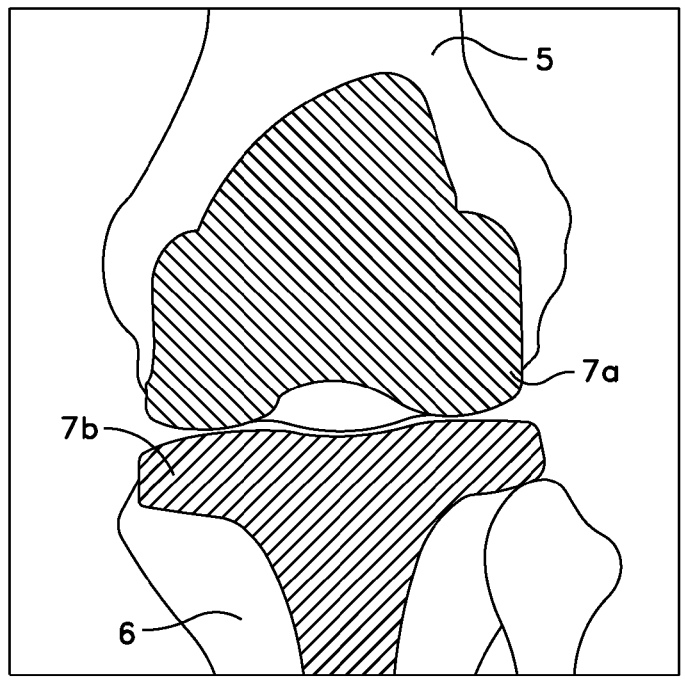
FIG. 7 is a schematic representation similar to FIGS. 4, 5, and 6, showing a digital representation of the femoral and tibial prostheses (in cross section) superimposed within the model in accordance with the present invention.
Figure 8:
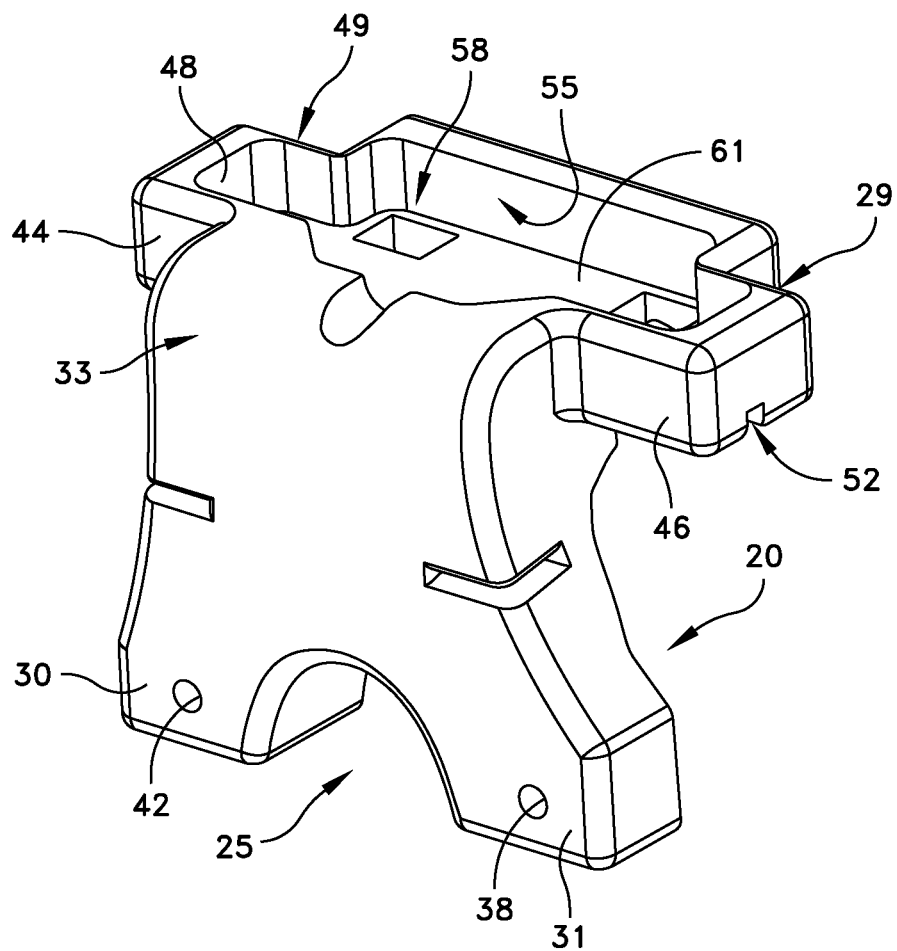
FIG. 8 is a perspective view of a femoral resection guide locator formed in accordance with the present invention.
Figure 9:
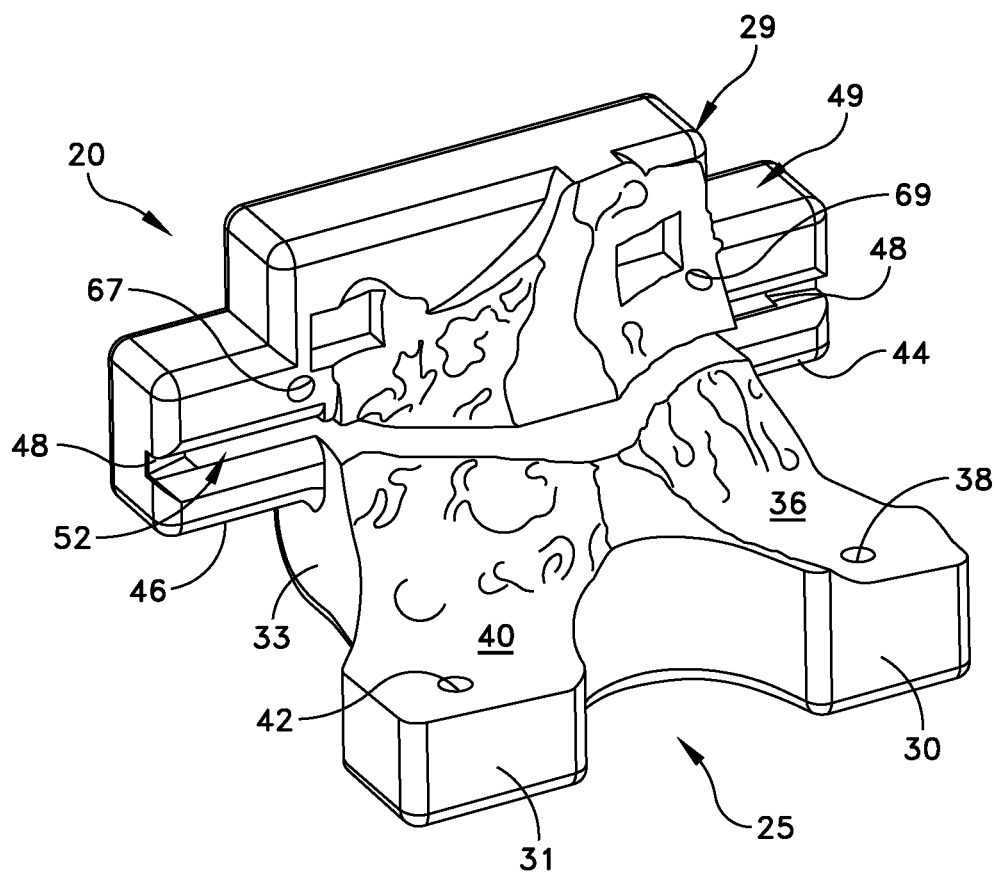
FIG. 9 is a rear perspective view of the femoral resection guide locator shown in FIG. 8.
Figure 10:
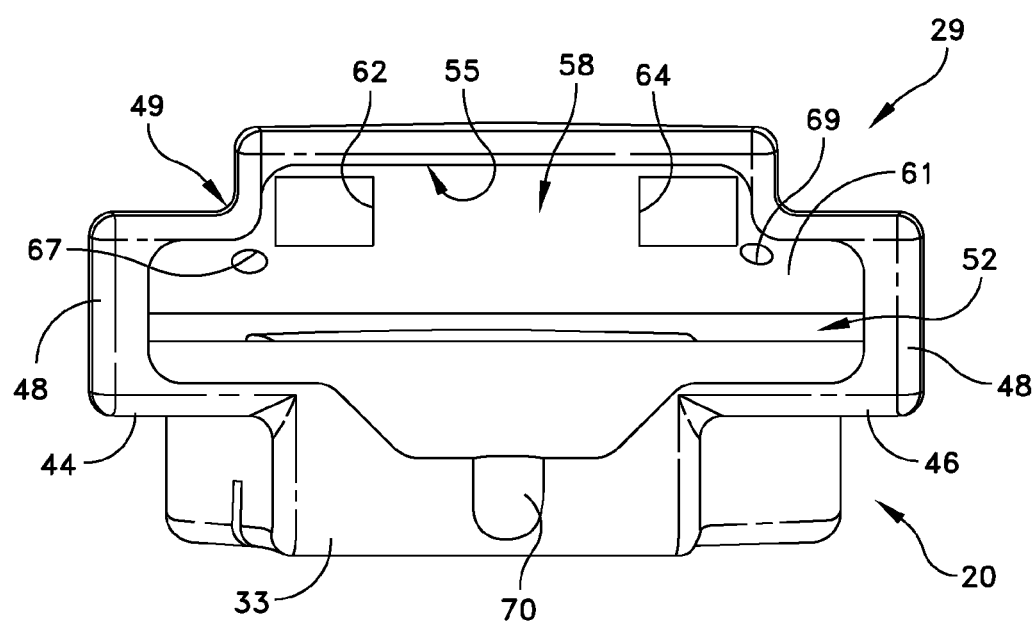
FIG. 10 is an elevational view of the front side of the femoral resection guide locator shown in FIG. 9.
Figure 11:
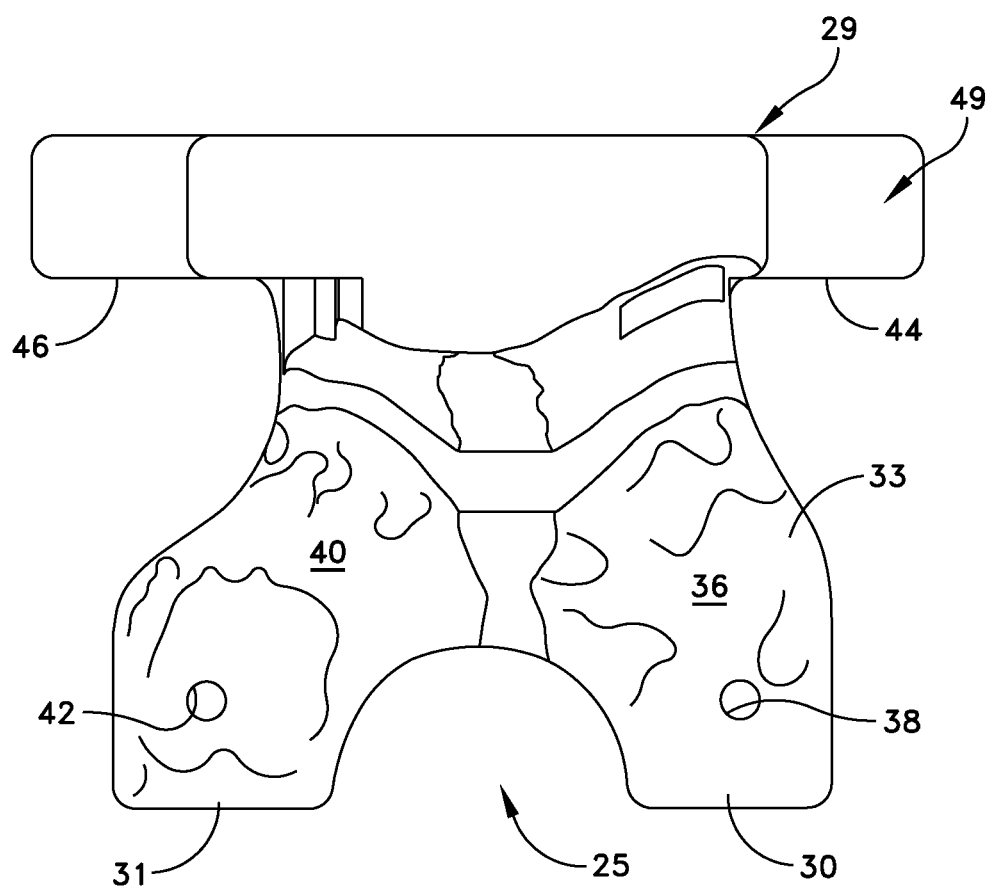
FIG. 11 is an elevational view of the bottom of the femoral resection guide locator shown in FIGS. 9 and 10.
Figure 12:
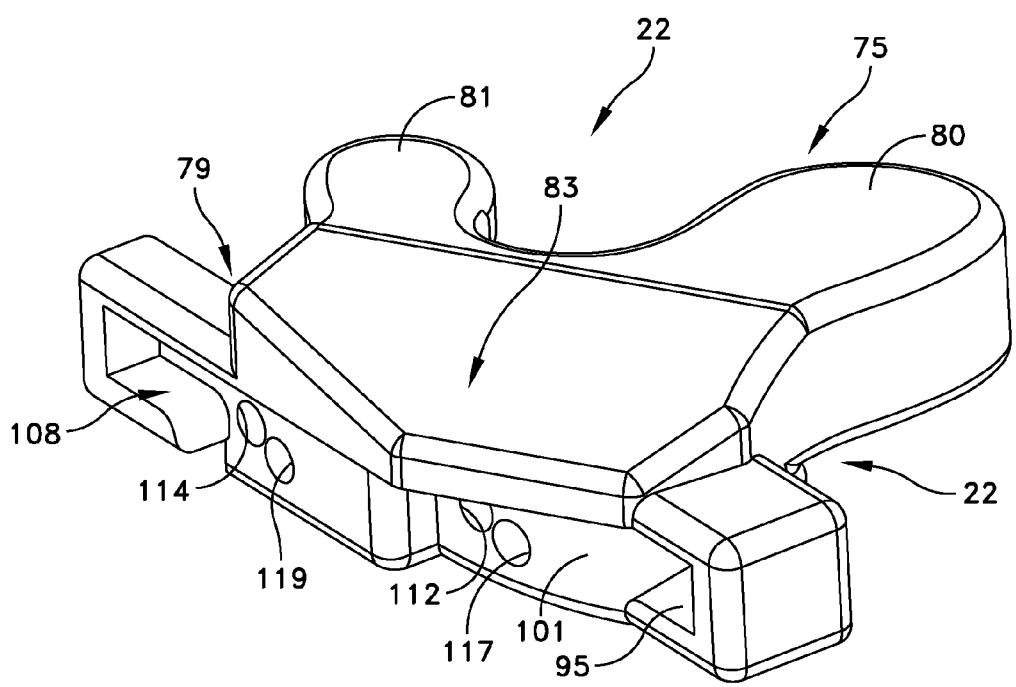
FIG. 12 is a perspective view of a tibial resection guide locator formed in accordance with the present invention.
Figure 13:
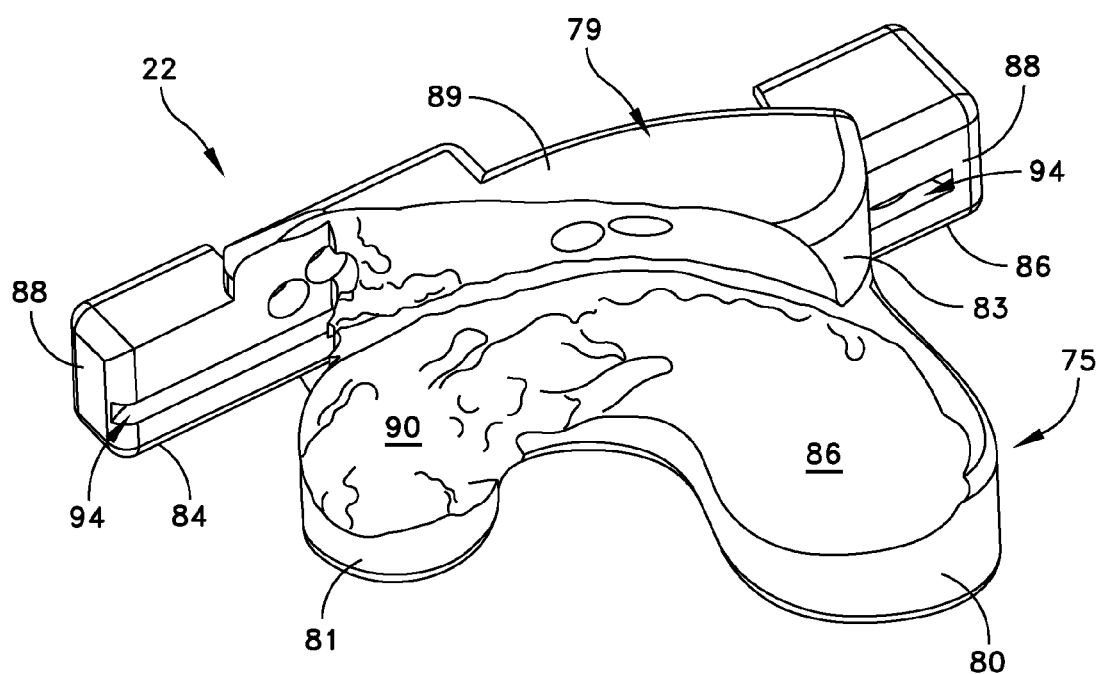
FIG. 13 is a perspective bottom view of the tibial resection guide locator shown in FIG. 12.
Figure 14:
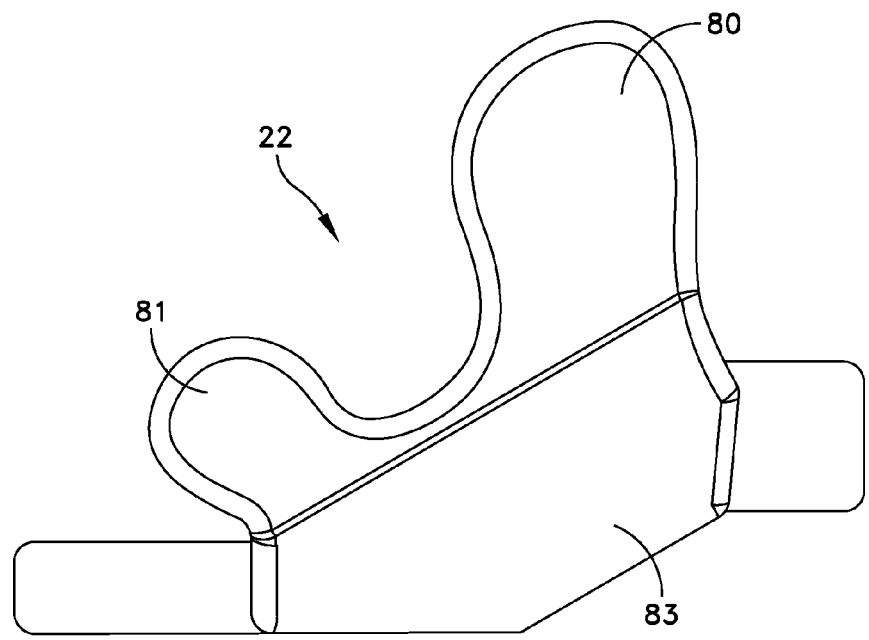
FIG. 14 is a top view of the tibial resection guide locator shown in FIG. 13.
Figure 15:
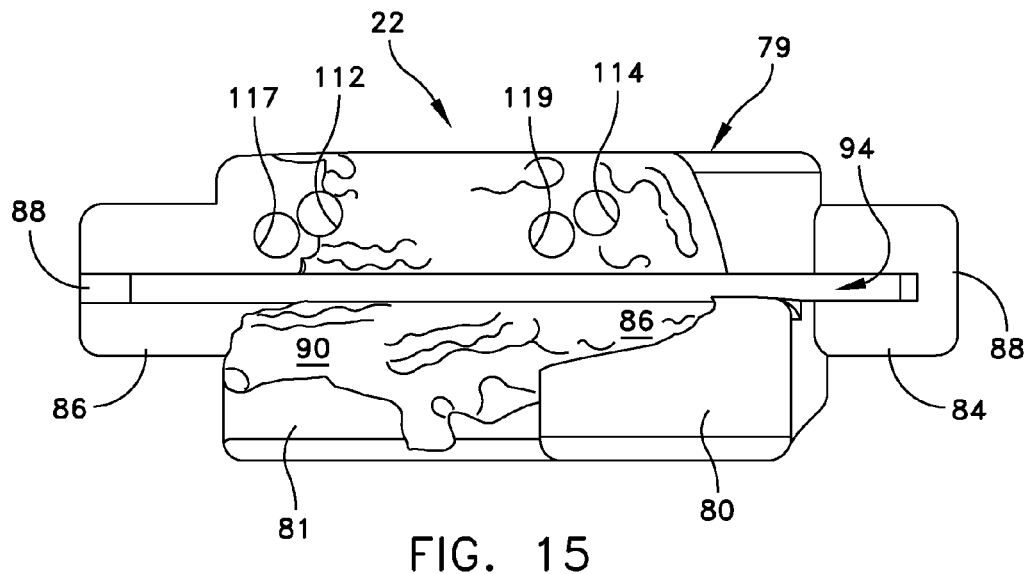
FIG. 15 is a rear elevational view of the tibial resection guide locator shown in FIG. 14.
Figure 16:
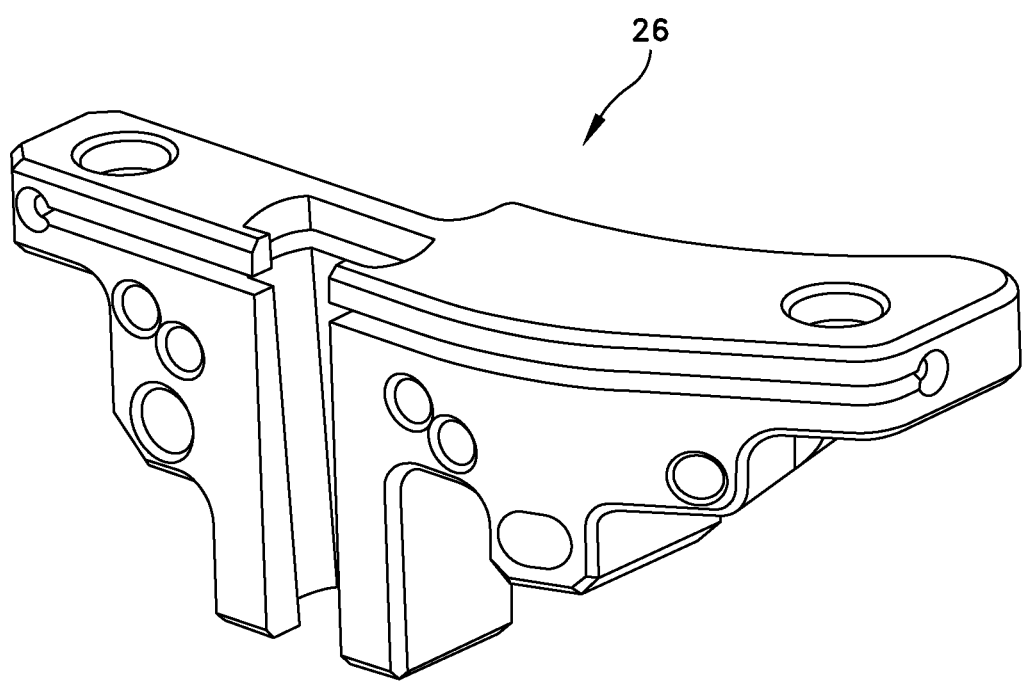
FIG. 16 is a perspective view of a typical tibial resection guide.
Figure 17:
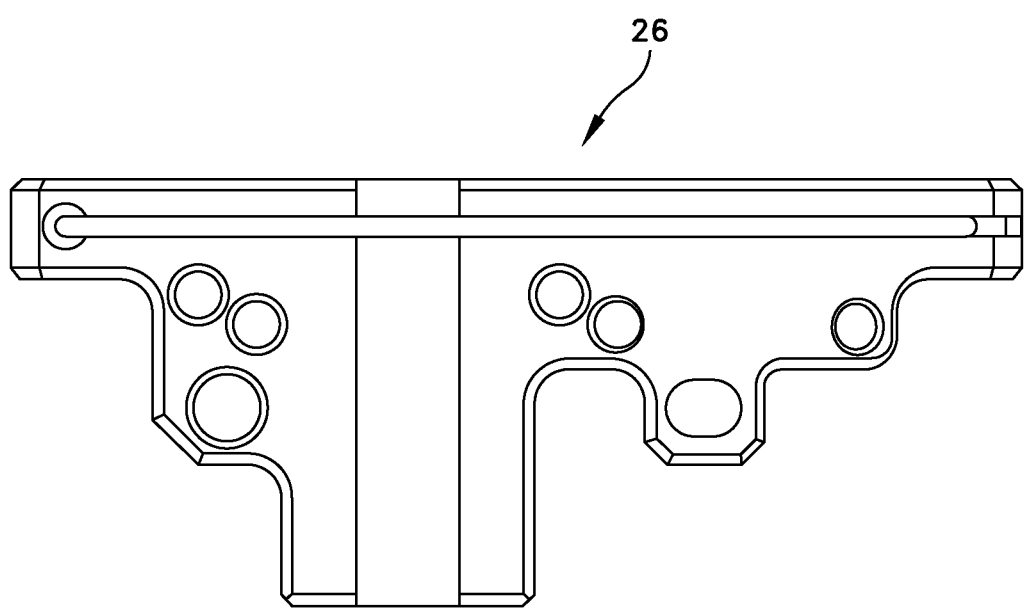
FIG. 17 is a front elevational view of the tibial resection guide shown in FIG. 16.
Figure 18:
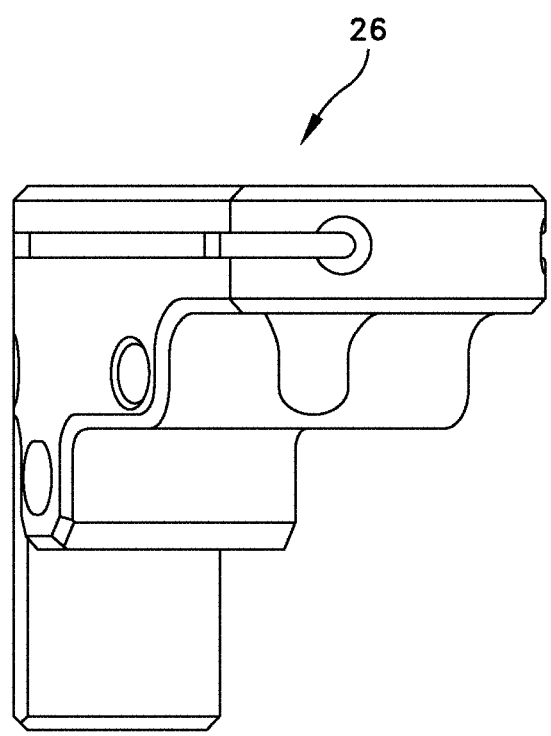
FIG. 18 is a side perspective view of the tibial resection guide shown in FIG. 17.

In accordance with the present invention, interactive processing and preparation of the digitized image data is performed which includes the manipulation and introduction of additional extrinsic digital information 8, such as, predefined reference locations 9 for component positioning and alignment 10 so that adjustments to the surgical site, that will require resection during surgery, may be planned and mapped onto computer model 3 (FIGS. 4 and 5). After the interactive processing of the digitized image data, it is possible to go back to original CAD data to obtain a higher resolution digital representation of the patient specific surgical instrument, prostheses 7a, 7b (FIG. 7) guide, or fixture so as to add that digital representation to the patient's image data model.

Figure 6:
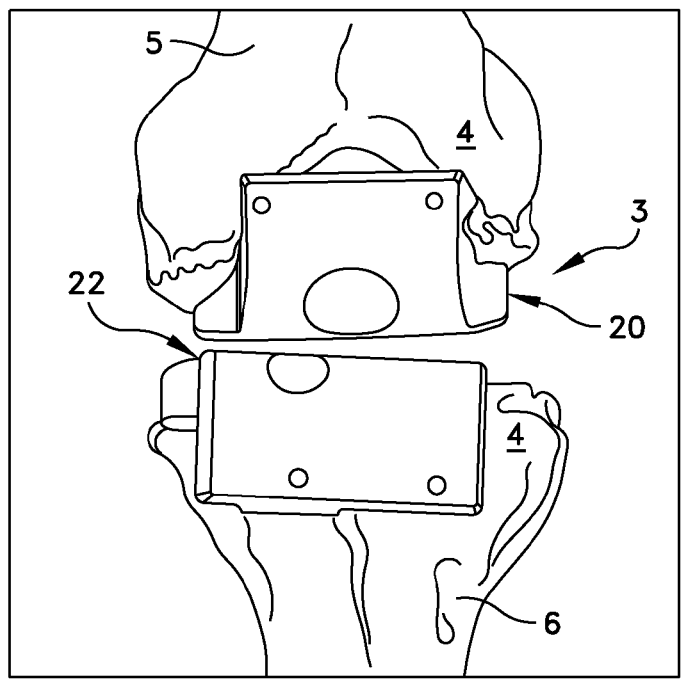
FIG. 6 is a schematic representation similar to FIGS. 4 and 5, but showing a femoral and a tibial resection guide locator represented within the computer model of FIG. 3 in accordance with the present invention.

For example, when the system of the present invention is used for knee replacement surgery, a digital representation of a femoral resection guide mount 20 may be added to the patient's image data model (FIGS. 1 and 6). In the context of a total knee replacement, femoral resection guide mount 20 may be formed for placement on the exposed condyles of a patient's femur to assure precise and accurate positioning of a femoral resection guide 26 which is used to direct and control bone resection of femur 5 during surgery. Although the femoral resection guide 26 can take various forms and configurations, the present invention will be described with reference to a distal resection guide currently offered by applicant Wright Medical Technology, Inc. (Wright Medical Part No. K001-2659). Significantly, femoral resection guide mount 20 provides this precise and accurate positioning function without the need for other external fixtures or the use of an intramedullary stem inserted through the intercondylar notch and upwardly through femur 5 along the femoral shaft axis. A digital representation of a tibial resection guide mount 22 may also be added to the patient's image data model (FIG. 6). Tibial resection guide mount 22 is similarly formed for placement on the exposed superior articular surface of a patient's tibia 6 to assure precise and accurate positioning of a tibial resection guide 28 used to direct and control bone resection of the superior articular surface of the exposed tibia during surgery.

Referring to FIGS. 8-11, a femoral resection guide mount 20 according to one embodiment of the invention is formed from a resilient polymer material of the type that is suitable for use in connection with stereo lithography, selective laser sintering, or the like manufacturing equipment. Resection guide mount 20 comprises a unitary block including a bifurcated condylar yoke 25 and a guide receptacle 29. Bifurcated yoke 25 includes a pair of spaced apart arms 30, 31 that project outwardly from a base 33. Arm 30 has a lower or bone engaging surface 36 and a through-bore 38, and arm 31 has a lower or bone engaging surface 40 and a through-bore 42. Through the previously discussed imaging operations, the bone engaging surfaces 36, 40 are configured for complementary matching with anatomical surface features of a selected region of the patient's natural bone. For the femoral resection guide mount 20 embodiment of FIGS. 8-11, the selected bone region comprises the condyles of the patient's femur.

Guide receptacle 29 includes a pair of wings 44,46 that project outwardly, in opposite directions from base 33 and in spaced relation to arms 30,31. Each wing 44, 46 includes a pylon 48 projecting upwardly to support guide housing 49 such that an elongate slot 52 is defined between base 33 and guide housing 49. Slot 52 is sized and shaped to allow a typical surgical saw, of the type often used for bone resection, to pass through from a correspondingly positioned and sized slot in resection guide 26 without contact, or with only incidental contact with resection guide locator 20. An annular wall 55, having a shape that is complementary to the outer profile of femoral resection guide 26, projects outwardly in substantially perpendicular relation to a back wall 61 and thereby defines a recess 58. In some preferred embodiments, recess 58 is sized so as to accept femoral resection guide 26 with a "press-fit". By press-fit it should be understood that annular wall 55 is sufficiently resilient to deflect or compress elastically so as to store elastic energy when femoral resection guide 26 is pushed into recess 58. Of course, it will also be understood that femoral resection guide 26 will have an outer circumferential shape that is complementary to the circumferential shape of recess 58, but slightly larger in size, for press-fit embodiments. Also, femoral resection guide 26 may be retained within recess 58 by only frictional engagement with annular wall 55 or, in less preferred embodiments, resection guide 26 can simply slide into recess 58 without operative contact or only incidental engagement with annular wall 55. First through-bores 62, 64 are defined in back wall 61 in spaced relation to one another, with a second through-bore 67,69 being associated with each first through-bore 62,64. In the embodiment shown in FIGS. 8-11, the first through-bores 62, 64 are large square or rectangular openings, a configuration that eases manufacture, reduces material use, and provides sufficient space for driving pins, wires, screws or other appropriate fasteners through a plurality of adjacent bores provided on the femoral resection guide 26. A groove 70 is defined in the outer surface of base 33 and centrally located with respect to recess 58 for matching to resection guide 26.

Referring to FIGS. 12-18, a tibial resection guide mount 22 according to one embodiment of the invention is formed from a resilient polymer material of the type that is suitable for use in connection with stereo lithography, selective laser sintering, or the like manufacturing equipment, e.g., a polyamide powder repaid prototype material is suitable for use in connection with selective laser sintering. Resection guide mount 22 comprises a unitary block including a bifurcated yoke 75 and a guide receptacle 79. Bifurcated yoke 75 includes a pair of spaced apart arms 80, 81 that project outwardly from a base 83. Arm 80 has a lower surface 86 and arm 81 has a lower surface 90.

Guide receptacle 79 includes a pair of wings 84, 86 that project outwardly, in opposite directions from base 83 and in spaced relation to arms 80,81. Each wing 84,86 includes a pylon 88 projecting upwardly to support guide housing 89 such that an elongate slot 94 is defined between base 83 and guide housing 89. Slot 94 is sized and shaped to allow a typical surgical saw, of the type often used for bone resection, to pass through from a correspondingly positioned and sized slot in resection guide 28 without contact, or with only incidental contact with resection guide locator 22. An annular wall 95, having a shape that is complementary to the outer profile of tibial resection guide 28, projects outwardly in substantially perpendicular relation to a back wall 101 and thereby defines a recess 108. Recess 108 is sized so as to accept tibial resection guide 28 with a press-fit. First through-bores 112, 114 are defined in back wall 101 in spaced relation to one another, with a second through-bore 117, 119 being associated with each first through-bore 112, 114.

Returning to the digital image models 3 previously disclosed, and considering a generalized digital model of resection guide mount 20 added to the patient's femur image data, the anatomic surface features of the patient's femur, e.g., the condylar surface topography, may be complementarily mapped onto each of lower surface 36 and lower surface 40 of arms 30, 31. It will be understood that complementary mapping of the digital images results in localized prominences on the surface of a bone, e.g., a condyle, cortical, or articular surface, becoming localized concavities on lower surface 36 or lower surface 40, while localized concavities on the surface of a bone become localized prominences on lower surface 36 or lower surface 40. In this way, each of lower surface 36 and lower surface 40 is redefined with a complementary, substantially mirror image of the anatomic surface features of a selected region of the patient's femur. As a consequence of this complementary bone surface mapping, resection guide mount 20 releasably "locks" on to the complementary topography of the corresponding portion of the patient's natural femur, e.g., the condylar surfaces, without the need for other external or internal guidance fixtures. In other words, the mating of bone surface asperities in their corresponding concavities formed in conformal bone engaging surfaces of femoral resection guide mount 20 ensures that little or no relative movement, e.g., slipping sideways, occurs between femoral resection guide mount 20 and the condylar surface. A substantially identical mapping is carried out in connection with the design of a patient specific tibial resection guide mount 22.

Figure 19:
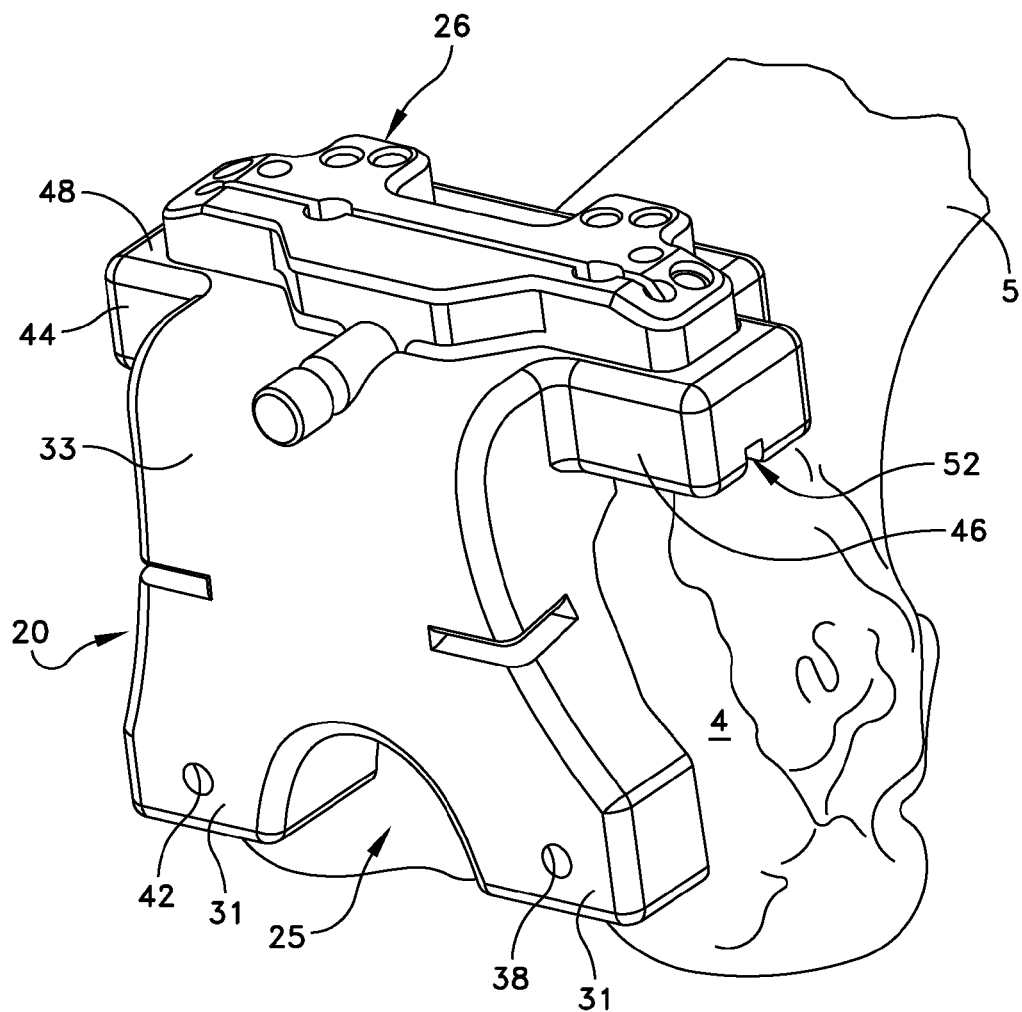
FIG. 19 is a perspective view of a femoral resection guide mounted within a femoral resection guide locator positioned upon the condyles of a femur.
Figure 20:
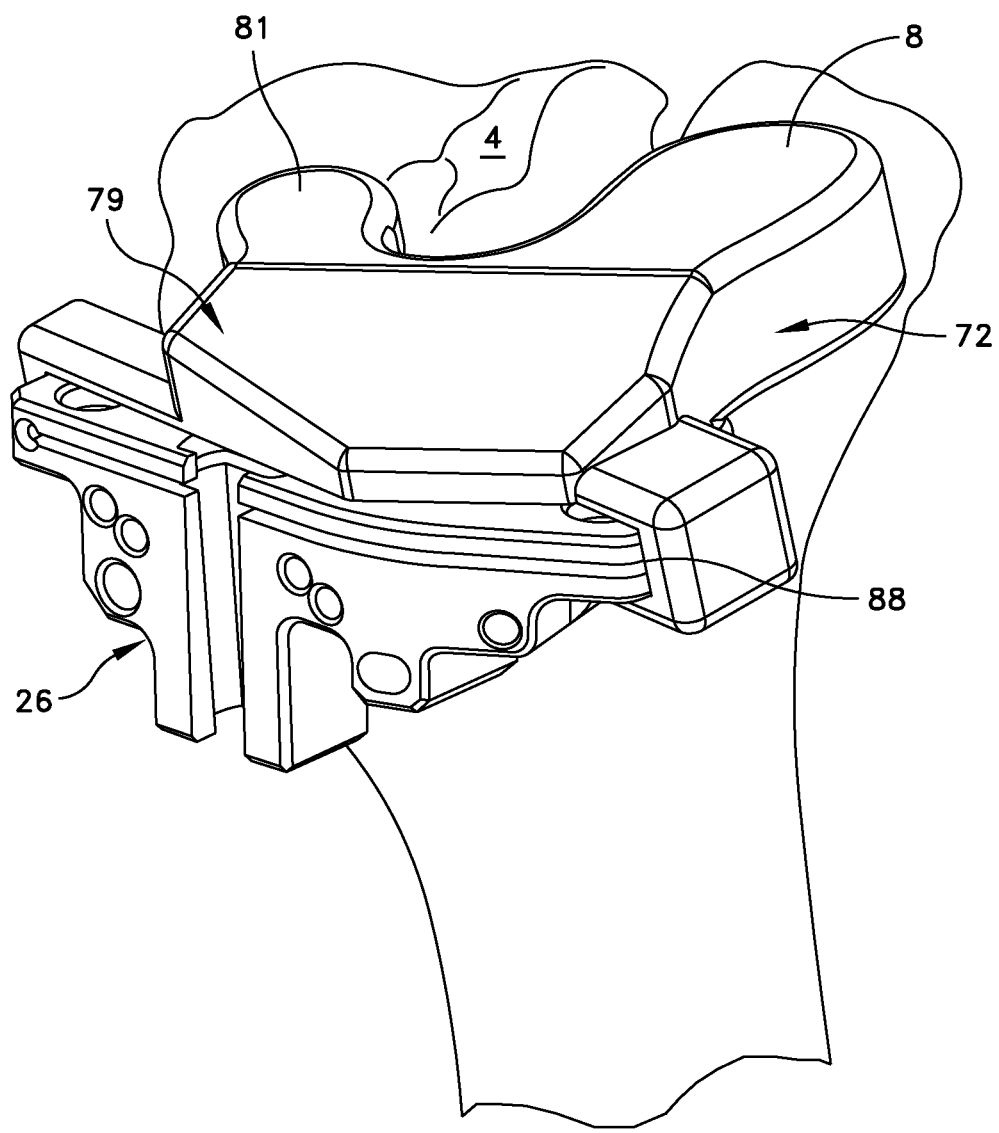
FIG. 20 is a perspective view of a tibial resection guide mounted within a tibial resection guide locator positioned upon the articular surfaces of a tibia.

A visual presentation of the virtual alignment results between the patient's femur and resection guide mount 20 is created and forwarded to the surgeon to obtain approval of the results prior to manufacturing (FIGS. 1, 19, 20). Upon receipt of the surgeon's approval, resection guide mount 20, and in appropriate instances resection guide mount 22, is manufactured and returned to the surgeon for use in the surgery.

During a total knee replacement the present invention is used in the following manner. The surgeon first orients resection guide mount 20 on femur 5 until lower surfaces 36, 40 of resection guide mount 20 securely engage one another so as to releasably "interlock" with the topography of the exposed surface 4 of femur 5. With resection guide mount 20 locked onto the patient's femur, a surgeon press-fits an appropriately configured Distal Resection Guide 26 (e.g. Wright Medical Technology, Inc. Part No. K001-2659) in recess 58 of resection guide mount 20. As indicated in FIGS.

19-20, this results in the resection guide mount 20, and particularly the guide receptacle portion 29 of the resection guide mount 20, being sandwiched between the resection guide 26 and the patient's bone. Pins are driven into through-bores of the resection guide 26, but advantageously the pins do not come into contact with the portions of resection guide mount 20 that define through-bores 62, 64 or 67, 69. These through-bores are often the most proximal on resection guide mount 20. With resection guide mount 20 held securely in place, a drill bit is advanced into through-bores 38 and 42, through-bores 62, 64 defined in back wall 61, and/or into second through-bores 67,69. It is often preferable for the drill to protrude about 15 mm into through-bores 38 and 42 into the femoral bone so the drill holes will be present after the distal resection. Increased hole depth may be necessary in the event of a larger distal resection to correct a flexion contracture. For additional stability, fixation pins (not shown) may be left in through-bores 38 and 42, but must be removed prior to resection. With the resection guide mount 20 thus accurately positioned with respect to the selected bone region and the resection guide 26-guide mount 20 construct appropriately secured to the patient's bone, the surgeon uses a conventional surgical blade and the resection slot of the resection guide 26 to resect the patient's bone.

Figure 22:
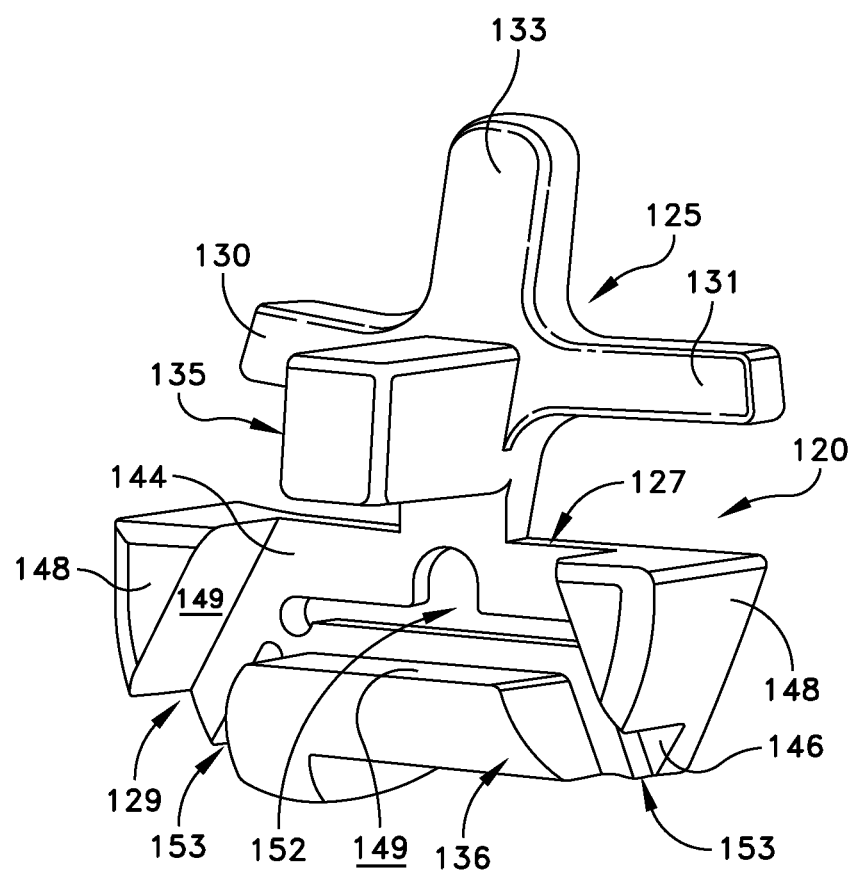
FIG. 22 is a perspective view of a tibial resection guide locator formed in accordance with the present invention.
Figure 26:
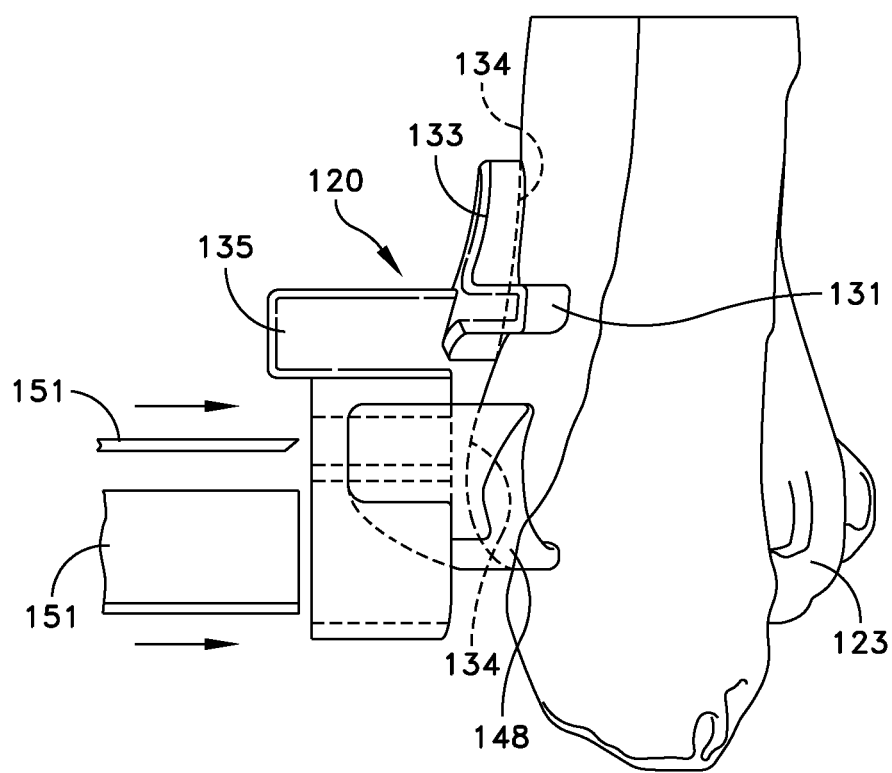
FIG. 26 is an exploded side elevational view of a tibial resection guide and tibial resection guide locator formed in accordance with the present invention located upon the lower portion of a tibia.

When the system of the present invention is used for ankle replacement surgery, a tibial resection guide mount 120 and a talar resection guide mount 122 are formed and mounted to the patient's lower tibia 123 and upper talus 124, respectively, in much the same way as femoral resection guide mount 20 and tibial resection guide mount 22. More particularly, a tibial resection guide mount 120 according to one embodiment of the invention is formed from a resilient polymer material of the type that is suitable for use in connection with stereo lithography or the like manufacturing equipment (FIG. 22). Resection guide mount 120 comprises a unitary body including a cruciform tibial yoke 125 projecting upwardly from a base 127 that further defines a guide receptacle recess 129. Cruciform yoke 125 includes a pair of spaced apart arms 130, 131 that project outwardly from a central post 133. Arms 130, 131 and central post 133 each have a conformal bone engaging surface 134 that is complementary to the contours of a corresponding portion of the patient's lower tibia (FIG. 26). Through the previously discussed imaging operations, conformal bone engaging surfaces 134 of arms 130, 131 and central post 133 are configured for complementary matching with anatomical surface features of a selected region of the patient's natural bone. For tibial resection guide mount 120, the selected bone region comprises the lower surfaces of the patient's tibia.

Figure 21:
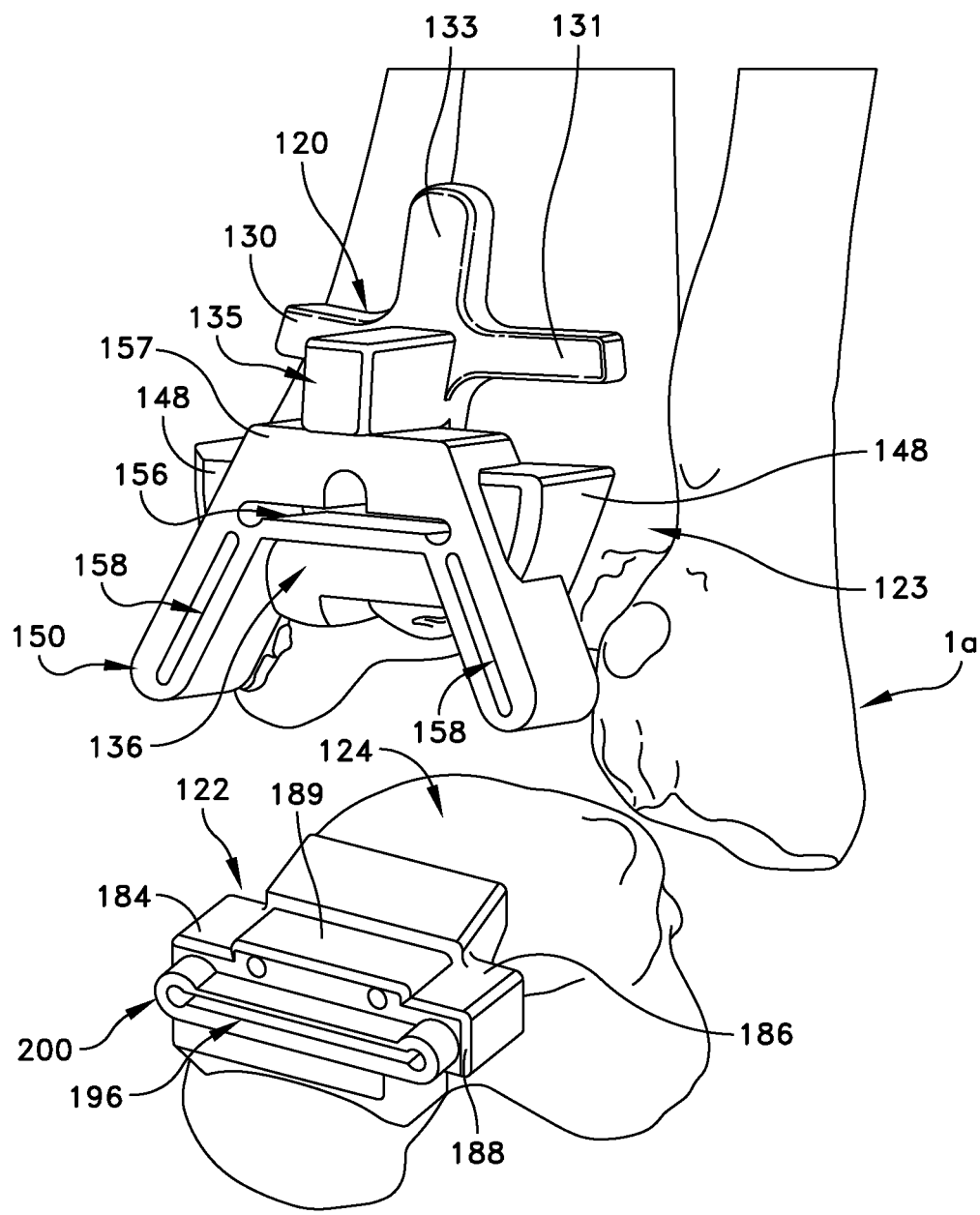
FIG. 21 is a perspective view of tibial and talar resection guides mounted within resection guide locators that have been formed in accordance with the present invention and located upon portions of a tibia and a talus, respectively.

A pilot block 135 projects outwardly from central post 133, adjacent to the intersection of arms 130,131. A support block 136 is located on base 127 in spaced relation to pilot block 135. Guide receptacle recess 129 is defined by a pair of wings 144,146 extend outwardly from either side of central post 133 in opposite directions on base 127, with support block 136 located between them. Each wing 144, 146 includes a pylon 148 projecting outwardly from base 127 so as to provide lateral support for tibial resection guide 150 (FIGS. 21 and 22). An elongate slot 152 is defined transversely in a central portion of base 127 below pilot block 135, but above support block 136. Each wing 144, 146 also defines a slot 153 that is oriented at an angle relative to central post 133. Slots 152 and 153 are sized and shaped to allow a typical surgical saw 151 (FIG. 26) of the type often used for bone resection, to pass through from a correspondingly positioned and sized slot in resection guide 150 without contact, or with only incidental contact with resection guide locator 120.

Figure 23:
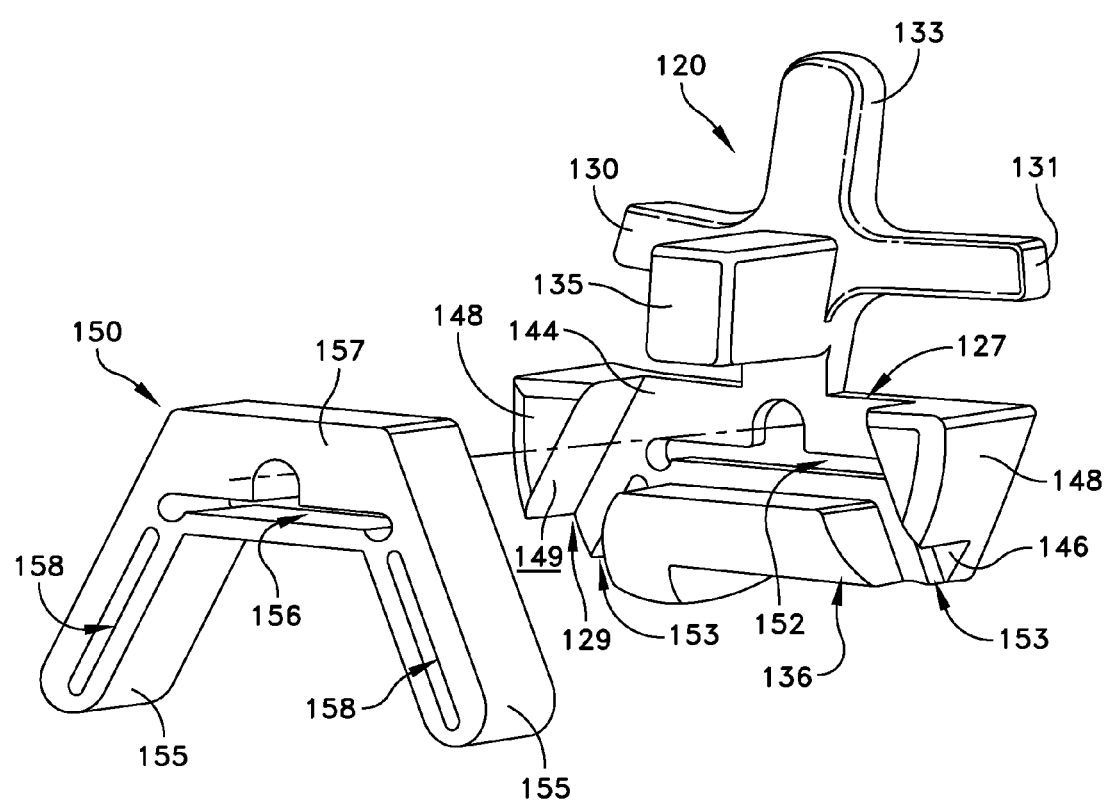
FIG. 23 is an exploded perspective view of a tibial resection guide and tibial resection guide locator formed in accordance with the present invention.

Referring to FIGS. 21 and 23, tibial resection guide 150 includes a pair of arms 155 that project downwardly and outwardly in diverging angular relation from the ends of a bridge beam 157. In this way, the shape of tibial resection guide 150 is complementary to the shape of guide receptacle recess 129 as defined by the inwardly facing surfaces of pilot block 135, support block 136, and pylons 148. Bridge beam 157 defines an elongate slot 156 and arms 155 each define a slot 158 that are, when assembled to resection guide mount 120, coextensively aligned with elongate slot 152 and slots 153, respectively in base 127. The inwardly facing surfaces 149 of pilot block 135, support block 136, and pylons 148, that together define guide receptacle recess 129, have a shape that is complementary to the outer profile of tibial resection guide 150. In some preferred embodiments, guide receptacle recess 129 is sized so as to accept tibial resection guide 150 with a "press-fit". By press-fit it should be understood that the inwardly facing surfaces 149 of pilot block 135, support block 136, and pylons 148 are sufficiently resilient to deflect or compress elastically so as to store elastic energy when tibial resection guide 150 is pushed into guide receptacle recess 129. Of course, it will also be understood that tibial resection guide 150 will have an outer peripheral shape that is complementary to the circumferential shape of guide receptacle recess 129, but slightly larger in size, for press-fit embodiments. Also, tibial resection guide 150 may be retained within guide receptacle recess 129 by only frictional engagement with the inwardly facing surfaces of pilot block 135, support block 136, and pylons 148 or, in less preferred embodiments, tibial resection guide 150 can simply slide into guide receptacle recess 129 without operative contact or only incidental engagement with the inwardly facing surfaces of pilot block 135, support block 136, and pylons 148.

Referring to FIGS. 21 and 28-33, a talar resection guide mount 122 according to one embodiment of the invention is formed from a resilient polymer material of the type that is suitable for use in connection with stereo lithography, selective laser sintering, or the like manufacturing equipment, e.g., a polyamide powder repaid prototype material is suitable for use in connection with selective laser sintering. Talar resection guide mount 122 also includes a conformal bone engaging surface 137 that is complementary to the contours of a corresponding portion of the patient's upper talus 124 (FIGS. 21, 28, and 31-34). Through the previously discussed imaging operations, conformal bone engaging surface 137 of talar resection guide mount 122 is configured for complementary matching with anatomical surface features of a selected region of the patient's natural bone. For talar resection guide mount 122, the selected bone region comprises the outer, upper surfaces of the patient's talus.

Figure 30:
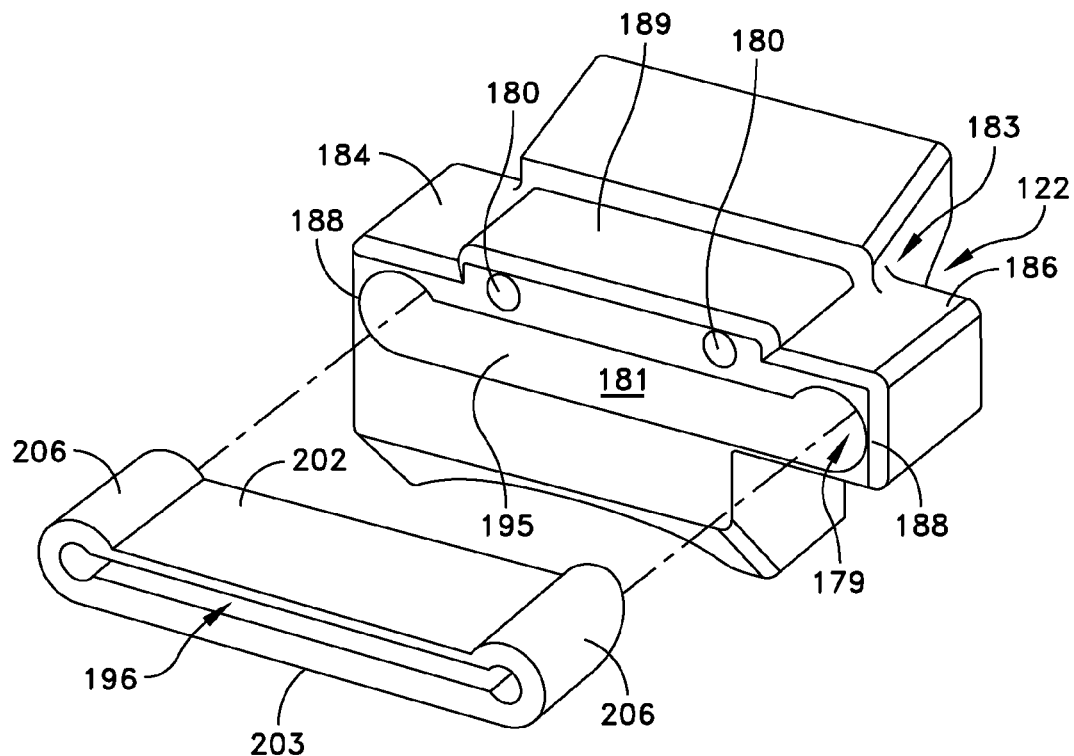
FIG. 30 is an exploded perspective view of a talar resection guide and talar resection guide locator formed in accordance with the present invention.
Figure 31:
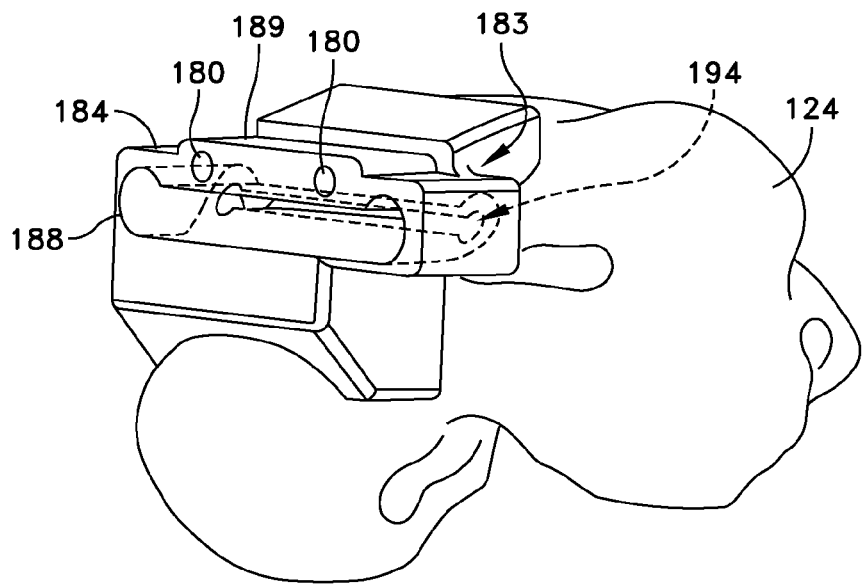
FIG. 31 is a perspective view of a talar resection guide locator formed in accordance with the present invention located on a talus bone of an ankle.
Figure 32:
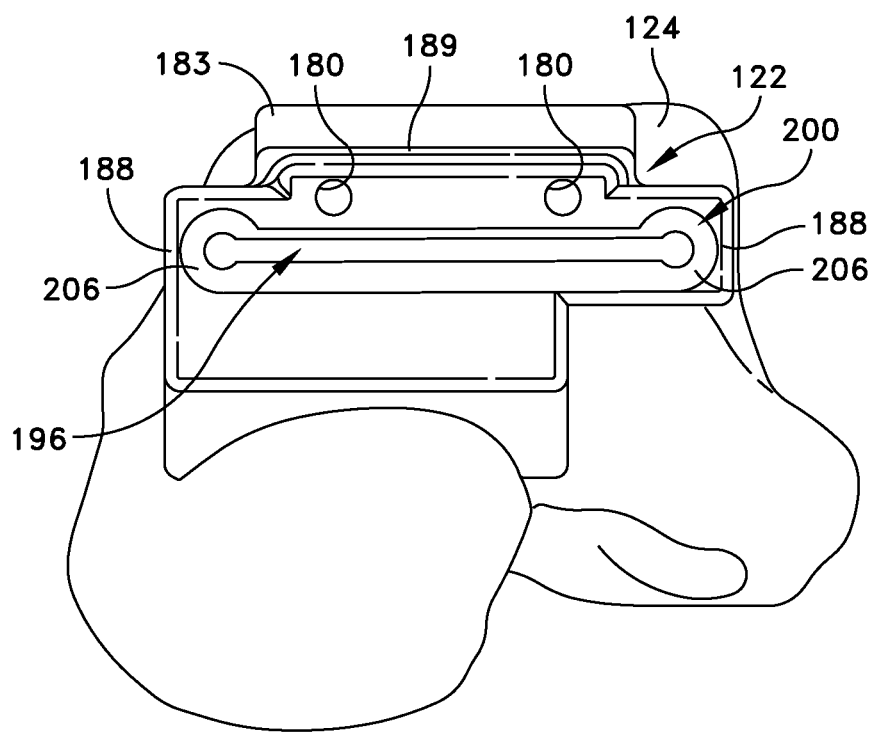
FIG. 32 is a front elevational view of a talar resection guide mounted within a resection guide locator that have been formed in accordance with the present invention and located upon the frontal portion of a talus bone.
Figure 33:
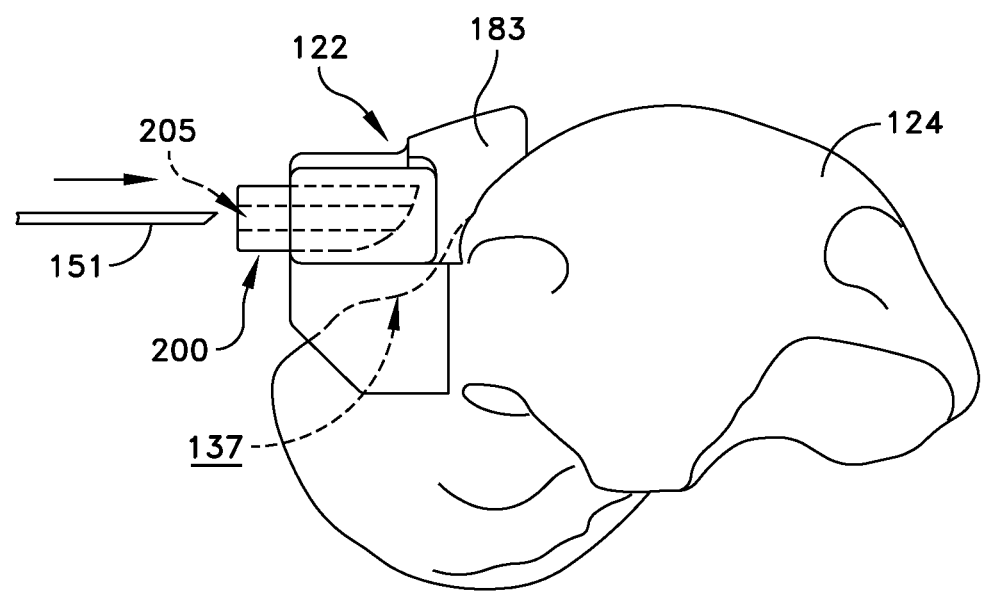
FIG. 33 is an exploded side elevational view of a talar resection guide and a talar resection guide locator formed in accordance with the present invention located upon the upper portion of a talus.

Talar resection guide mount 122 comprises a unitary block that defines a central guide receptacle recess 179 and a pair of through-bores 180 (FIG. 30). Guide receptacle recess 179 is defined by the inwardly facing surfaces 181 of a pair of wings 184, 186 that project outwardly, in opposite directions from a base 183. Each wing 184,186 includes a pylon 188 projecting upwardly to support guide housing 189 such that an elongate slot 194 is defined within base 183 and below guide housing 189 (FIGS. 31 and 33). Slot 194 is sized and shaped to allow a typical surgical saw 151, of the type often used for bone resection, to pass through from a correspondingly positioned and sized slot 196 in talar resection guide 200 without contact, or with only incidental contact with talar resection guide locator 122. An annular wall 195, having a shape that is complementary to the outer profile of talar resection guide 200, projects outwardly in substantially perpendicular relation to a back wall and so as to further defines guide receptacle recess 179.

Figure 28:
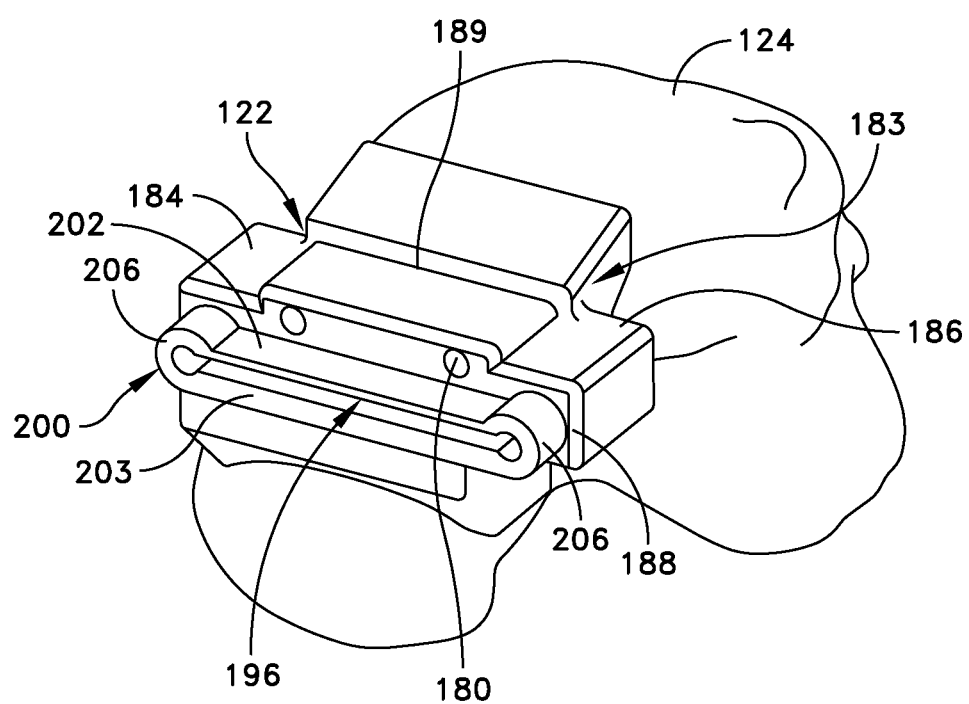
FIG. 28 is a perspective view of a talar resection guide mounted within a talar resection guide locator that have been formed in accordance with the present invention and located upon a portion of a talus.
Figure 29:
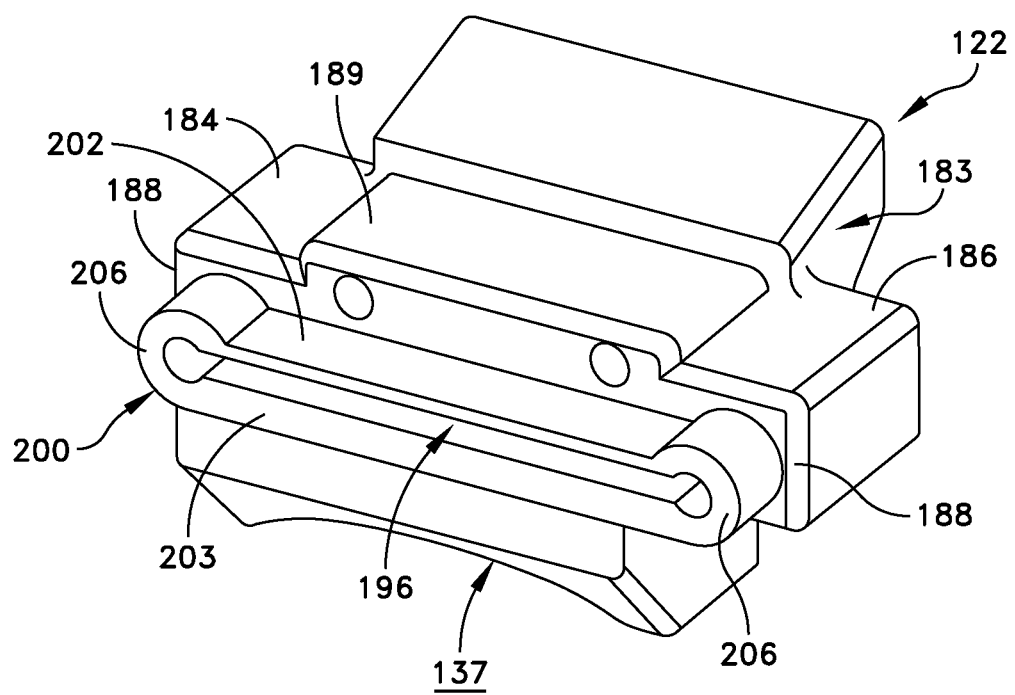
FIG. 29 is a perspective view of a talar resection guide mounted within a talar resection guide locator formed in accordance with the present invention.

Referring to FIGS. 28, 29, and 30, talar resection guide 200 includes a pair of confronting, parallel plates 202, 203 that define elongate slot 196 between them, and are joined to one another at their ends by wings 206. In this way, the shape of talar resection guide 200 is complementary to the shape of guide receptacle recess 179 as defined by the inwardly facing surfaces 181 of wings 184, 186, base 183, and pylons 188. Guide receptacle recess 179 is sized so as to accept talar resection guide 200 with a press-fit. Of course, it will also be understood that talar resection guide 200 will have an outer peripheral shape that is complementary to the circumferential shape of guide receptacle recess 179, but slightly larger in size, for press-fit embodiments. Also, talar resection guide 200 may be retained within guide receptacle recess 179 by only frictional engagement with the inwardly facing surfaces 181 of wings 184, 186, base 183, and pylons 188 or, in less preferred embodiments, talar resection guide 200 can simply slide into guide receptacle recess 179 without operative contact or only incidental engagement with the inwardly facing surfaces 181 of wings 184, 186, base 183, and pylons 188.

As with the digital image models 3 previously disclosed, and considering a generalized digital model of a tibial resection guide mount 120 added to the patient's lower tibia image data, the anatomic surface features of the patient's lower tibia, e.g., the surface topography, may be complementarily mapped onto each of conformal bone engaging surfaces 134 of arms 130, 131 and central post 133, i.e., the surfaces that will engage the bones unique surface topography. It will be understood that complementary mapping of the digital images results in localized prominences on the surface of a bone becoming localized concavities on conformal bone engaging surfaces 134 of arms 130, 131 and central post 133, while localized concavities on the surface of a bone become localized prominences on conformal bone engaging surfaces 134 of arms 130, 131 and central post 133. In this way, each of conformal bone engaging surfaces 134 of arms 130, 131 and central post 133 is redefined with a complementary, substantially mirror image of the anatomic surface features of a selected region of the patient's lower tibia. As a consequence of this complementary bone surface mapping, tibial resection guide mount 120 releasably "locks" on to the complementary topography of the corresponding portion of the patient's natural tibia without the need for other external or internal guidance fixtures. In other words, the mating of bone surface asperities in their corresponding concavities formed in conformal bone engaging surfaces 134 of tibial resection guide mount 120 ensures that little or no relative movement, e.g., slipping sideways, occurs between tibial resection guide mount 120 and the tibial surface. A substantially identical mapping is carried out in connection with the design of a patient specific talar resection guide mount 122.

A visual presentation of the virtual alignment results between the patient's lower tibia and resection guide mount 120, as well as, the patients upper talus and resection guide mount 122 are created and forwarded to the surgeon to obtain approval of the results prior to manufacturing. Upon receipt of the surgeon's approval, resection guide mount 120 and resection guide mount 122, are manufactured and returned to the surgeon for use in the surgery.

Figure 24:
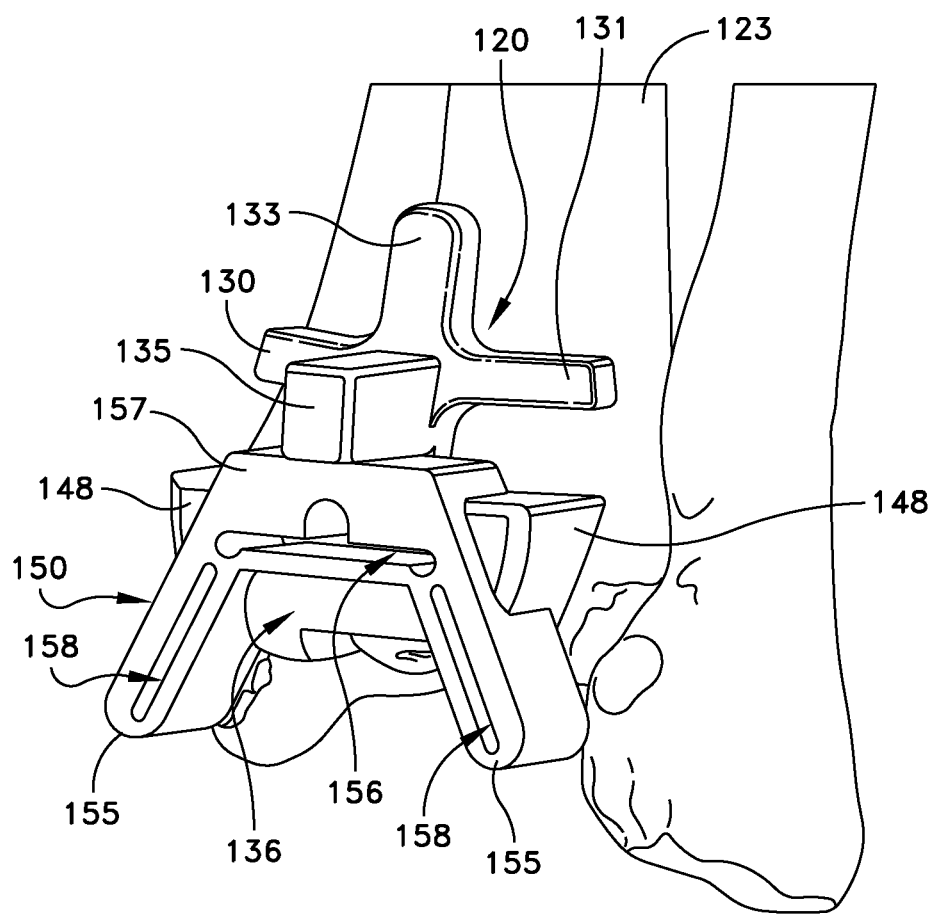
FIG. 24 is a perspective view of a tibial resection guide mounted within a resection guide locator that have been formed in accordance with the present invention and located upon the lower portion of a tibia.
Figure 25:
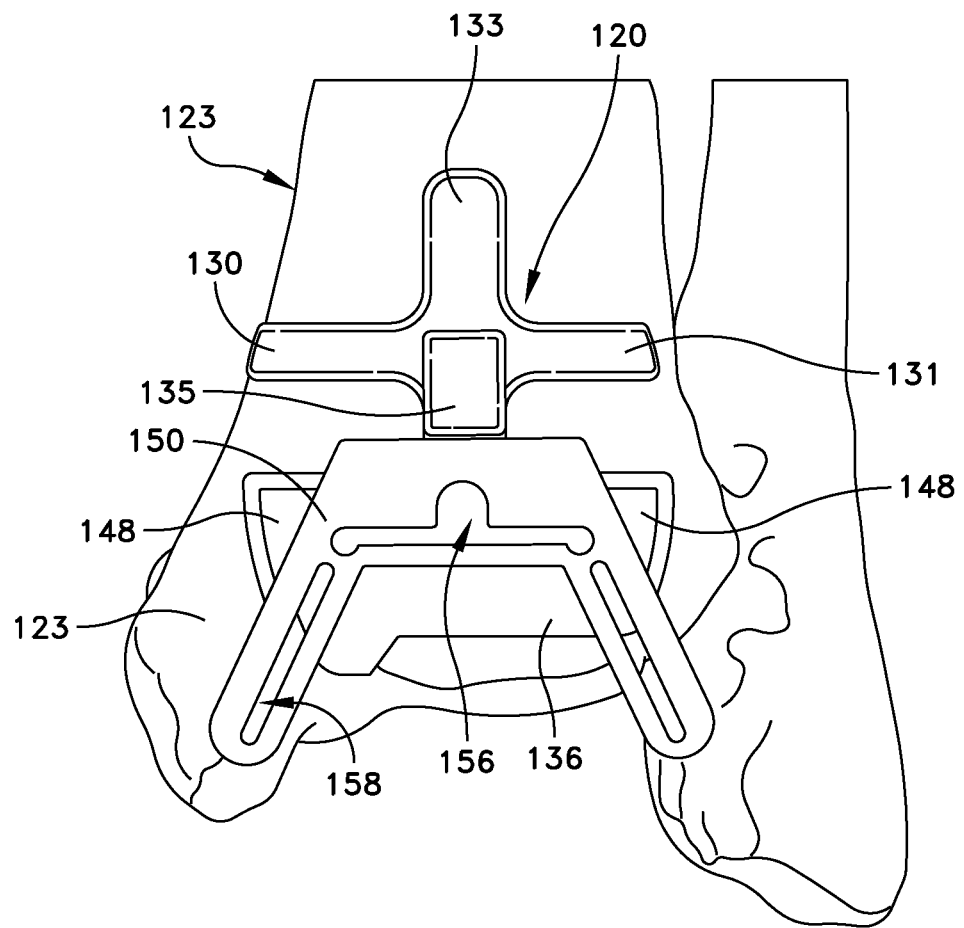
FIG. 25 is a front elevational view of a tibial resection guide mounted within a resection guide locator that have been formed in accordance with the present invention and located upon the distal portion of a tibia.
Figure 27:
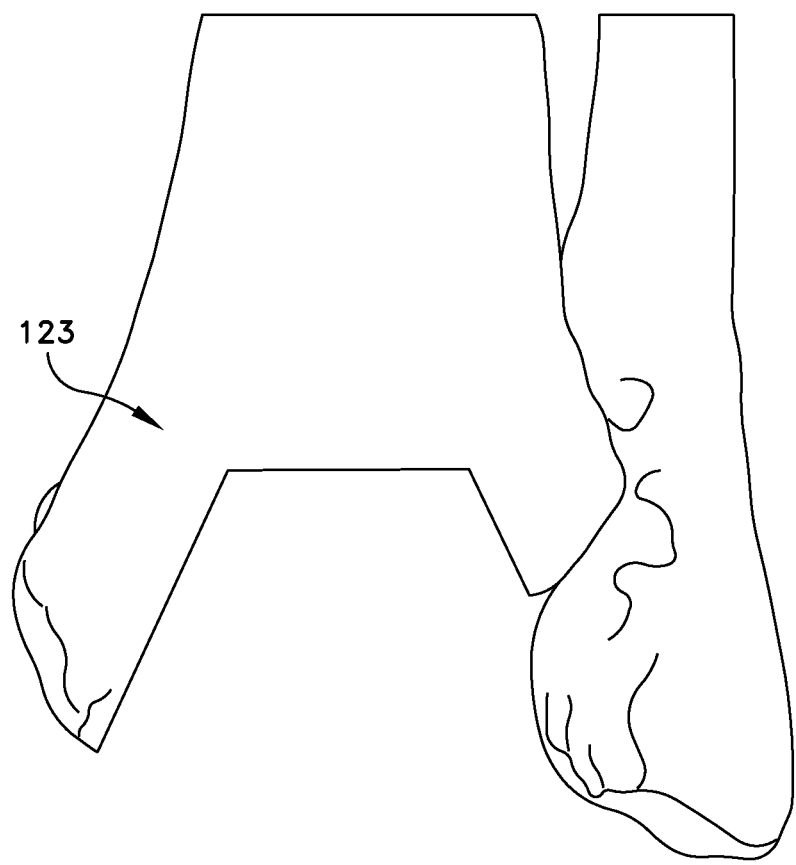
FIG. 27 is a schematic representation of a resected distal tibia following application and use of a tibial resection guide and tibial resection guide locator formed in accordance with the present invention.

During a total ankle replacement, the present invention is used in the following manner. The surgeon first orients resection guide mount 120 on lower tibia 123 until the conformal bone engaging surfaces 134 of arms 130, 131 and central post 133 of resection guide mount 120 securely engage one another so as to releasably "interlock" with the topography of the exposed surface of lower tibia 123. With resection guide mount 120 locked onto the patient's lower tibia, a surgeon press-fits an appropriately configured distal resection guide 150 in guide receptacle recess 129 of resection guide mount 120. This results in the resection guide mount 120 being sandwiched between the resection guide 150 and the patient's bone (FIGS. 21, 24, and 25). With the resection guide mount 120 accurately positioned with respect to the selected bone region and resection guide 150-guide mount 120 construct appropriately secured to the patient's bone by virtue of the mating of bone surface asperities in their corresponding concavities formed in conformal bone engaging surfaces 134, the surgeon uses a conventional surgical blade 151 and the resection slots 152 and 153 of resection guide 150 to resect the patient's bone (FIG. 27).

In a similar fashion, when talar resection guide mount 122 is added to the patient's talar image data, the anatomic surface features of the patient's upper talus, e.g., the surface topography, may be complementarily mapped onto conformal bone engaging surface 137. It will again be understood that complementary mapping of the digital images results in localized prominences on the surface of a bone becoming localized concavities on conformal bone engaging surface 137, while localized concavities on the surface of a bone become localized prominences on conformal bone engaging surface 137. In this way, conformal bone engaging surface 137 is redefined with a complementary, substantially mirror image of the anatomic surface features of a selected region of the patient's lower tibia. As a consequence of this complementary bone surface mapping, talar resection guide mount 122 releasably "locks" on to the complementary topography of the corresponding portion of the patient's natural talus without the need for other external or internal guidance fixtures.

Figure 34:
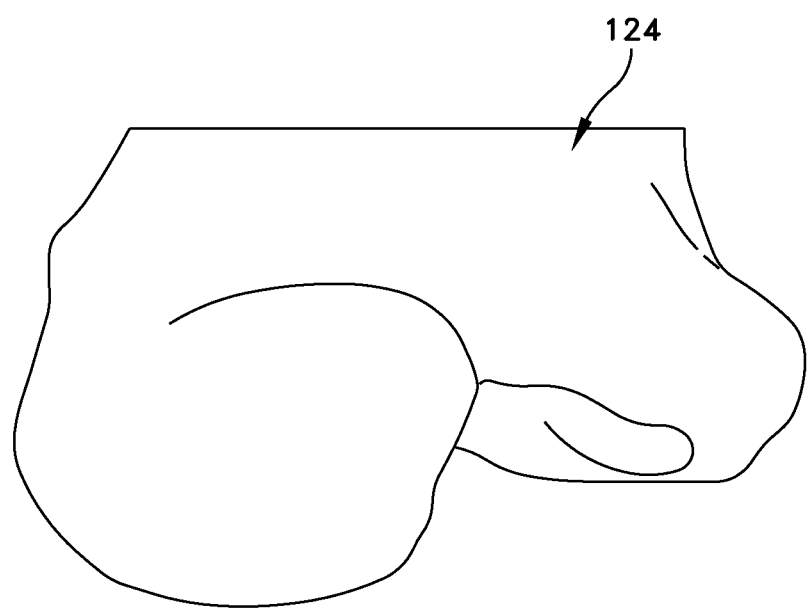
FIG. 34 is a schematic representation of a resected talar bone following application and use of a talar resection guide and talar resection guide locator formed in accordance with the present invention.

To continue the total ankle replacement the surgeon first orients resection guide mount 122 on upper talus 124 until conformal bone engaging surface 137 of resection guide mount 122 "locks" to the topography of the exposed surface of upper talus 124. With resection guide mount 122 locked onto the patient's upper talus, a surgeon press-fits an appropriately configured distal resection guide 200 in guide receptacle recess 179 of resection guide mount 122. This results in resection guide mount 122 being sandwiched between resection guide 200 and the patient's bone (FIGS. 21, 28, 32, and 33). With the resection guide mount 122 accurately positioned with respect to the selected bone region and resection guide 200-guide mount 122 construct appropriately secured to the patient's bone, by virtue of the mating of bone surface asperities in their corresponding concavities formed in conformal bone engaging surfaces 137, the surgeon uses a conventional surgical blade 151 and the resection slot 196 of resection guide 200 to resect the patient's bone (FIG. 34).

It is to be understood that the present invention is by no means limited only to the particular constructions herein disclosed and shown in the drawings, but also comprises any modifications or equivalents within the scope of the claims.

What is claimed is:

1. A resection system configured for making a distal resection of a bone of a femur, said bone having localized anatomical surface features prior to resection, comprising:
a resection guide locator including a body having a bone engagement portion with a surface comprising localized features that are topographically complementary to said localized anatomical surface features of said bone of said femur,
the body including opposing medial and lateral wings, the wings extending outwardly from the body,
the body defining a recess, the recess being a socket defined by an annular wall,
the annular wall including an upper wall, a lower wall, and opposing medial and lateral side walls, the medial and lateral side walls disposed between the upper and lower walls, the medial side wall disposed in the medial wing, the lateral side wall disposed in the lateral wing, the upper wall offset from the medial and lateral side walls such that a length of the upper wall is less than a distance between the medial and lateral side walls, and an elongate slot within the recess,
a resection guide having a body defining a resection slot, at least a portion of the resection guide body sized and configured to be received within the recess defined by the resection guide locator,
wherein the resection guide locator and the resection guide are formed from different materials, and wherein the resection slot defined by the resection guide aligns with the elongate slot defined by the resection guide locator when the resection guide is received within the recess defined by the resection guide locator, the resection slot positioned for making said distal resection of said bone of said femur when the resection guide is received within the recess of the resection guide locator.

2. The resection system of claim 1, wherein the resection guide locator includes a yoke including first and second arms that extend from the body in a direction that is different from the direction in which the pair of wings extend.

3. The resection system of claim 2, wherein each of the first and second arms defines a respective through bore.

4. The resection system of claim 3, wherein each wing of the pair of wings defines a respective through bore.

5. The resection system of claim 1, wherein the resection guide locator is formed from a resilient polymer material and the resection guide is formed from a metal.

6. The resection system of claim 1, wherein the localized features of the bone engagement portion are complementary to said localized anatomical surface features of an articular surface of said bone.

7. The resection system of claim 1, wherein the localized features of the bone engagement portion are complementary to said localized anatomical surface features of a condylar surface of said bone.

8. The resection system of claim 1, wherein the localized features of the bone engagement portion are complementary to said localized anatomical surface features of a cortical surface of said bone.

9. The resection system of claim 1, further comprising the recess having a back wall, the elongate slot formed through the back wall and extending between the opposing side walls.

10. The resection system of claim 1, further comprising the resection guide having a stem projecting downward therefrom, and the resection guide locator having a groove defined in an outer surface of the base below the lower wall, the groove configured for accommodating the stem of the resection guide.

11. The resection system of claim 10, wherein the groove is centrally located with respect to the recess.

12. The resection system of claim 1, wherein the upper wall of the annular wall adjoins the medial side wall via an L-shaped portion of the annular wall and further adjoins the lateral side wall via an opposing L-shaped portion of the annular wall.

* * * * *